US006270749B1

(12) United States Patent
Blumenkranz et al.

(10) Patent No.: US 6,270,749 B1
(45) Date of Patent: *Aug. 7, 2001

(54) USE OF TEXAPHYRIN IN OCULAR DIAGNOSIS AND THERAPY

(75) Inventors: Mark S. Blumenkranz, Portola Valley; Kathryn W. Woodburn, Sunnyvale; Richard A. Miller; Stuart W. Young, both of Portola Valley, all of CA (US)

(73) Assignee: Pharmacyclics, Inc., Sunnyvale, CA (US)

(*) Notice: Subject to any disclaimer, the term of this patent is extended or adjusted under 35 U.S.C. 154(b) by 0 days.

(21) Appl. No.: 09/329,720

(22) Filed: Jun. 10, 1999

Related U.S. Application Data

(63) Continuation of application No. PCT/US97/22661, filed on Dec. 11, 1997
(60) Provisional application No. 60/093,058, filed on Dec. 11, 1996.

(51) Int. Cl.$^7$ .......................... A61K 49/00; A01N 55/02
(52) U.S. Cl. ........................ 424/9.61; 424/9.6; 514/185; 514/912
(58) Field of Search .................... 424/9.61, 9.6, 424/427; 514/427, 185, 912; 540/145, 465, 472; 534/10–16

(56) References Cited

U.S. PATENT DOCUMENTS

| | | | |
|---|---|---|---|
| 5,166,197 | 11/1992 | Kenney et al. | 514/63 |
| 5,252,720 | 10/1993 | Sessler et al. | 534/11 |
| 5,266,302 | 11/1993 | Peyman et al. | 424/9 |
| 5,346,689 | 9/1994 | Peyman et al. | 424/7.1 |
| 5,484,778 | 1/1996 | Kenney et al. | 514/63 |
| 5,576,013 | 11/1996 | Williams et al. | 424/423 |
| 5,599,923 | * 2/1997 | Sessler et al. | 540/145 |
| 5,756,541 | 5/1998 | Strong et al. | 514/502 |
| 5,775,339 | 7/1998 | Wodburn et al. | 128/898 |
| 5,913,884 | 6/1999 | Trauner et al. | 607/88 |
| 6,008,211 | * 12/1999 | Robinson et al. | 514/185 |

FOREIGN PATENT DOCUMENTS

| | | | |
|---|---|---|---|
| 0 407 122 A1 | 1/1991 | (EP) | C12P/21/02 |
| WO 95/24930 | 9/1995 | (WO) | A61K/49/04 |
| WO 97/05127 | 2/1997 | (WO) | C07D/309/38 |
| WO 97/33619 | 9/1997 | (WO) | A61K/31/40 |
| WO 97/35617 | 10/1997 | (WO) | A61K/41/00 |
| WO 97/46262 | 12/1997 | (WO) | A61K/47/48 |
| WO 98/11827 | 3/1998 | (WO) | A61B/17/00 |
| WO 98/25648 | 6/1998 | (WO) | A61K/41/00 |

OTHER PUBLICATIONS

American Academy of Ophthalmology, "Macular Degeneration —Major Cause of Central Vision Loss" (1982).
American Academy of Ophthalmology, World Wide Web Page entitled "Focus on Macular Degeneration," Webmaster@aao.org, May 1996.
Asrani, Sanjay and Ran Zeimer, "Feasibility of laser targeted photo–occlusion of ocular vessels," *British Journal of Ophthalmology*, 79:766–770, 1995.
Baumal, et al., "Photodynamic Therapy of Experimental Choroidal Neovascularization with Tin Ethyl Etiopurpurin", *Investigative Ophthalmology & Visual Science*, Feb. 15, 1996, vol. 37, No. 3 (581–B493) Abstract.
Crean, et al., "Photodynamic Therapy Response of Choriocapillaris Using Tin Ethyl Etiopurpurin", *Investigative Ophthalmology & Visual Science*, Feb. 15, 1996, vol. 37, No. 3 (582–B5294) (Abstract).
Elman, Michael J. and Stuart L. Fine, "Exudative age–related macular degeneration," *Macular Disease*, 2:175–200, 1989.
Guyer, et al., "Digital Indocyanine–green Angiography in Chorioretinal Disorders," *Ophthalmology*, 99:287–291, 1992.
Hungerford, J.L., "Management of Ocular Melanoma," *British Medical Bulletin*, 51:694–716, 1995.
Husain, D. and Joan W. Miller, "Photodynamic Therapy of Exudative Age–Related Macular Degeneration," *Seminars in Ophthalmology*, vol. 12, No. 1 (Mar.), pp. 14–25, 1997.
Kliman, et al., "Phthalocyanine Photodynamic Therapy: New Strategy for Closure of Choroidal Neovascularization," Lasers in Surgery and Medicine, 15 : 2–10, 1994.
Kliman, et al., "Retinal and Choroidal Vessel Closure Using Phthalocyanine Photodynamic Therapy," Lasers in Surgery and Medicine, 15 : 11–18, 1994.
Levy, Julia G., "Photosensitizers in Photodynamic Therapy," Seminars in Oncology, vol. 21, No. 6, Suppl. 15, pp. 4–10, Dec. 1994.
Lin, et al., "Photodynamic Closure of Choroidal Vessels Using Benzoporphyrin Deriviative"; IOVS 34:1303, Abstract 2953, 1993.
McCartney, A.C.E., "Pathology of ocular melanomas," *British Medical Bulletin*, 51:678–693, 1995.
Miller, et al., "Phthalocyanine Photodynamic Therapy of Experimental Iris Neovascularization," *Ophthalmology*, vol. 98, No. 11, pp. 1711–1719, Nov. 1991.

(List continued on next page.)

Primary Examiner—Michael G. Hartley
(74) Attorney, Agent, or Firm—Vinit G. Kathardekar

(57) ABSTRACT

The use of texaphyrins for ocular diagnosis and therapy is provided, especially use of photosensitive texaphyrins for photodynamic therapy of conditions of the eye characterized by abnormal vasculature, such as macular degeneration, or pterygium, for example. The photosensitive texaphyrin may be a free-base texaphyrin or may be metallated with a diamagnetic metal. Preferably, the photosensitive texaphyrin is metallated with lutetium. Due to the dual wavelength absorption of texaphyrins, i.e., at 400–500 nm and at 700–800 nm, especially about 732 nm, as compared to porphyrins, texaphyrins are more effective and versatile for use in humans as compared to porphyrins. Texaphyrins serve as effective contrast agents in ocular angiography.

32 Claims, 4 Drawing Sheets

OTHER PUBLICATIONS

Obana et al., Photodynamic Therapy of Choroidal Vessels Using a Newly–Developed Chlorin Derivative *Investigative Ophthalmology & Visual Science*, Feb. 15, 1996, vol. 37 No 3, 579–B491 (Abstract).

PDT Inc.—Press release "PDT Inc. and IRIDEX to co–develop devices for photodynamic therapy in ophthalmology", May 29, 1996.

PDT Inc.—Press release PDT Inc. awarded NIH research grant in ophthalmology, Jun. 17, 1996.

PDT Inc.—Press release PDT Inc. and Pharmacia & Upjohn sign co–development agreement for ophthalmology; the companies will co–develop SnET2 in photodynamic therapy for serious eye diseases., Aug. 28, 1996.

Peyman, et al., "Photodynamic Therapy for Choriocapillaris Using Tin Ethyl Etiopurpurin (SnET2) ," Ophthalmic Surgery and Lasers, vol. 28, No. 5, pp. 409–417, May 1997.

Schmid Erfurth, et al, Photdynamic therapy of Subfoveal Choroidal Neovascularization Using Benzoporphyrin Derivative: first Results of a Multi–Center Trial, *Investiative Ophthalmology & Visual Science*, Feb. 15, 1996, vol. 37, No 3, 580–B492 (Abstract).

Young, et al., "Lutetium Texaphyrin (PCI–0123) : A Near–Infrared, Water–Soluble Photosensitizer," *Photochemistry and Photobiology*, 63(6) : 892–897, 1996.

* cited by examiner

USE OF TEXAPHYRIN IN OCULAR DIAGNOSIS AND THERAPY

This application is a continuation application of international application PCT/US97/22661 filed Dec. 11, 1997, which claims priority to U.S. Ser. No. 60/093,058, filed Dec. 11, 1996. The applications are incorporated by reference herein.

BACKGROUND OF THE INVENTION

The retina is a thin layer of light-sensitive tissue that lines the inside wall of the back of the eye. When light enters the eye, it is focused by the cornea and the lens onto the retina. The retina then transforms the light images into electrical impulses that are sent to the brain through the optic nerve.

The macula is a very small area of the retina responsible for central vision and color vision. The macula allows us to read, drive, and perform detailed work. Surrounding the macula is the peripheral retina which is responsible for side vision and night vision. Macular degeneration is damage or breakdown of the macula, underlying tissue, or adjacent tissue. Macular degeneration is the leading cause of decreased visual acuity and impairment of reading and fine "close-up" vision. Age-related macular degeneration (ARMD) is the most common cause of legal blindness in the elderly.

The most common form of macular degeneration is called "dry" or involutional macular degeneration and results from the thinning of vascular and other structural or nutritional tissues underlying the retina in the macular region. A more severe form is termed "wet" or exudative macular degeneration. In this form, blood vessels in the choroidal layer (a layer underneath the retina and providing nourishment to the retina) break through a thin protective layer between the two tissues. These blood vessels may grow abnormally directly beneath the retina in a rapid uncontrolled fashion, resulting in oozing, bleeding, or eventually scar tissue formation in the macula which leads to severe loss of central vision. This process is termed choroidal neovascularization (CNV).

CNV is a condition that has a poor prognosis; effective treatment using thermal laser photocoagulation relies upon lesion detection and resultant mapping of the borders. Angiography is used to detect leakage from the offending vessels but often CNV is larger than indicated by conventional angiograms since the vessels are large, have an ill-defined bed, protrude below into the retina and can associate with pigmented epithelium.

Neovascularization results in visual loss in other eye diseases including neovascular glaucoma, ocular histoplasmosis syndrome, myopia, diabetes, pterygium, and infectious and inflammatory diseases. In histoplasmosis syndrome, a series of events occur in the choroidal layer of the inside lining of the back of the eye resulting in localized inflammation of the choroid and consequent scarring with loss of function of the involved retina and production of a blind spot (scotoma). In some cases, the choroid layer is provoked to produce new blood vessels that are much more fragile than normal blood vessels. They have a tendency to bleed with additional scarring, and loss of function of the overlying retina. Diabetic retinopathy involves retinal rather than choroidal blood vessels resulting in hemorrhages, vascular irregularities, and whitish exudates. Retinal neovascularization may occur in the most severe forms.

Current diagnosis of ocular disorders often includes use of a dye such as fluorescein or indocyanine green in an angiogram. Fluorescein is a low molecular weight molecule that rapidly leaks from vessels, however, due to its low absorption and emission wavelengths and due to autofluorescence, only superficial morphology can be imaged; subretinal hemorrhage blocks the detection of the underlying chorioretinal vasculature. In contrast, ICG, having an absorption band at 805 nm and fluorescence at 835 nm, is able to image deeper choroidal vessels better than fluorescein due to spectral differences and also due to its longer retainment in the diseased vasculature, possibly in association with albumin. In this procedure, the dye is injected into the blood stream through a vein in the arm. Special filters are placed in the light path, and in front of the film, to permit the fluorescent dye to be seen as it passes through the vessels in the retina Pictures of the vascular anatomy are taken of the retina and macula as the dye passes through the blood vessels of the back of the eye. Vascular occlusions or leakage of dye generally indicates abnormal vasculature, however, a problem with fluorescein is that of leakage. Optical coherence tomography is another technique that uses noncontact imaging and provides high-depth resolution in cross-sectional tomographs of the retina.

Current treatment of neovascularization relies on ablation of blood vessels using thermal laser photocoagulation. However, such treatment is nonselective, requires thermal destruction of the tissue, and is accompanied by full-thickness retinal damage, as well as damage to medium and large choroidal vessels. Further, the patient is left with an atrophic scar and visual scotoma. Moreover, recurrences are common, and the prognosis for the patient's condition is poor.

Developing strategies have sought more selective closure of the blood vessels to preserve the overlying neurosensory retina. One such strategy is photodynamic therapy (PDT), a treatment technique that uses a photosensitizing dye and non-damaging light corresponding to the sensitizer's absorption profile to produce cytotoxic materials, such as singlet oxygen, from benign precursors when irradiated in the presence of oxygen.

Other reactive species such as superoxide, hydroperoxyl, or hydroxyl radicals may be involved in the consequent irreversible damage to biological components. At the doses used, neither the light nor the drug has any independent activity against the target.

The effectiveness of PDT is predicated on three additional factors: i) The photosensitive dyes used in PDT preferably have the ability to localize at the treatment site as opposed to surrounding tissue. ii) The high reactivity and short lifetime of activated oxygen means that it has a very short range (~0.1 $\mu$m) and is unlikely to escape from the region in which it is produced; cytotoxicity is therefore restricted to the precise region of photoactivated drug. iii) Developments in light delivery, such as lasers, light emitting diodes, and fiber optics, allow a beam of intense, non-damaging, light to be delivered accurately to many parts of the body. For a review of photodynamic therapy, see U.S. Pat. No. 5,252,720 (incorporated by reference herein).

Photodynamic therapy of conditions in the eye characterized by neovascularization has been attempted using conventional porphyrin derivatives such as hematoporphyrin derivative (dihematoporphyrin ether), PHOTOFRIN® porfimer sodium, and tin ethyl etiopurpurin. Problems have been encountered in this context due to interference from eye pigments, as described in U.S. Pat. No. 5,576,013 to Williams, et al. for example. In addition, phthalocyanine and benzoporphyrin derivatives have been used in photodynamic treatment. PCT publication WO 95/24930 and Miller et al., (*Archives of Ophthalmology*, June, 1995) relate to treatment of eye conditions characterized by unwanted neovasculature comprising administering a green porphyrin to the neovasculature and irradiating the neovasculature with light having a wavelength of 550–695 nm. U.S. Pat. No. 5,166,197 and 5,484,778 relate to phthalocyanine derivatives reportedly useful for macular degeneration. Asrani and Zeimer (*British Journal of Ophthalmology*, 1995, 79:766–770) relate to photoocclusion of ocular vessels using a phthalocyanine encapsulated in heat-sensitive liposomes. Levy (*Semin. Oncol.* 1994, 21/6, suppl. 15 (4–10)) relates to photodynamic therapy with porfimer sodium (PHOTOFRIN®, requiring light of 630 nm and causing cutaneous photosensitivity that may last for up to 6 weeks), and benzoporphyrin derivative (BPD verteporfin, causing cutaneous photosensitivity of a few days). Lin et al. (IOVS 34:1303 Abstract 2953, 1993) relate to the photodynamic occlusion of choroidal vessels using benzoporphyrin derivative BPD-MA. Baumal et al. (*Invest. OphthalmoL Vis. Sci.* 37/3:S122 (abstract) 1996) relates to PDT of experimental choriodal neovascularization with tin ethyl etiopurpurin (SnET2) and 665 nm irradiation. BPD and SnET2 are insoluble in aqueous solutions and require hydrophobic vehicles for administration. Further limitations of prior art photosensitizers include inadequate light penetration through hemorraghic and pigmented tissue, systenic cutaneous photosensitivity, lack of selectivity, normal tissue damage, and reopening of diseased vessels. Hydrophobic vehicle solubilizers require clearance time prior to irradiation. Bolus injection and instantaneous illumination cannot be performed.

Texaphyrins are aromatic pentadentate macrocyclic "expanded porphyrins" useful as MRI contrast agents, as radiosensitizers, as chemosensitizers, and in photodynamic therapy. Texaphyrin is considered as being an aromatic benzannulene containing both 18π- and 22π-electron delocalization pathways. Texaphyrin molecules absorb strongly in the tissue-transparent 700–900 nm range, and they exhibit inherent selective uptake or biolocalization in certain tissues, particularly regions such as, for example, liver, atheroma or tumor tissue. Texaphyrins have exhibited significant tumor selectivity as detected by magnetic resonance imaging and fluorescence detection. Texaphyrins and water-soluble texaphyrins, method of preparation and various uses have been described in U.S. Pat. Nos. 4,935,498; 5,162,509; 5,252,720; 5,256,399; 5,272,142; 5,292,414; 5,369,101; 5,432,171; 5,439,570; 5,451,576; 5,457,183; 5,475,104; 5,504,205; 5,525,325; 5,559,207; 5,565,552; 5,567,687; 5,569,759; 5,580,543; 5,583,220; 5,587,371; 5,587,463; 5,591,422; 5,594,136; 5,595,726; 5,599,923; 5,599,928; 5,601,802; 5,607,924; and 5,622,946; PCT publications WO 90/10633; 94/29316; 95/10307; 95/21845; 96/09315; 96/38461; 96/40253; 97/26915; and 97/35617; PCT application application PCT/US97/09501 published as WO 97/46262; allowed U.S. patent application Ser. No. 08/458, 347, issued as U.S. Pat. No. 5,798,491; Ser. No. 08/484,551, issued as U.S. Pat. No. 5,714,328; and Ser. No. 08/591,318, issued as U.S. Pat. No. 5,776,925; and U.S. patent application Ser. No. 08/763,451 converted to Ser. No. 60/093,058, now abandoned; Ser. No. 08/903,099, issued as U.S. Pat. No. 6,022,526; and Ser. No. 08/914,272, issued as U.S. Pat. No. 5,775,339; each patent, publication, and application is incorporated herein by reference.

The present invention provides texaphyrins for ocular diagnosis and therapy. The use of texaphyrins circumvents problems seen in prior art methods, in part, because of the dual wavelengths for absorption of light, solubility in aqueous solutions, rapid clearance, use of a bolus injection, and the provision of a single agent for visualization and treatment.

SUMMARY OF THE INVENTION

The present invention provides use of a texaphyrin in the preparation of a pharmaceutical composition for use in ocular diagnosis and therapy, in particular, therapy involving photodynamic therapy of conditions of the eye characterized by abnormal vasculature. Accordingly, an aspect of the invention is directed to use of a texaphyrin for carrying out angiography of the eye, i.e., observing vasculature of an eye of a subject. The method of use comprises the steps of administering a detectable texaphyrin to the subject and observing the vasculature state of the eye. When the detectable texaphyrin is fluorescent, observing may be by fluorescence; when the detectable texaphyrin is complexed with a paramagnetic cation, the observing may be by magnetic resonance imaging. Further, imaging of a detectable texaphyrin may be carried out using x-rays, Raman Scattering, magnetometry (bioluminescence) or optical coherence tomography. In a further aspect of the invention, use of a texaphyrin for treating an ocular condition of a subject characterized by abnormal vasculature is provided. The method of use comprises the steps of administering a photosensitive texaphyrin to the subject; and photoirradiating the vasculature. The method of use may further comprise the step of observing the ocular condition of the subject by imaging the texaphyrin as stated herein.

Use of a texaphyrin for photodynamic therapy of macular degeneration of a subject, the method of use comprising the steps of administering a photosensitive texaphyrin to the subject and photoirradiating the macula is another aspect of the invention.

Use of a texaphyrin for observing and treating an ocular condition of a subject characterized by abnormal vasculature using a single agent is also an aspect of the invention. The method of use comprises the steps of administering a photosensitive fluorescent texaphyrin to the subject, observing the ocular condition of the subject by fluorescence of the texaphyrin, and photoirradiating the vasculature.

For angiography, texaphyrins may be activated by 400–500 nm light (the Soret band) or 700–800 nm light (the Q band) and, therefore, provide considerable versatility for use in humans (see FIG. 1). For phototherapy, texaphyrins may be irradiated at 400–500 nm and at longer wavelengths of light where ocular tissues are relatively transparent, especially where light can penetrate blood and vascular tissue, i.e., 700–800 nm, especially at about 732 mn. Texaphyrins are particularly effective as visualizing agents in angiography of ocular blood vessels due to their localization in areas of abnormal permeability or damage. Texaphyrins are particularly effective in PDT in that the wavelength of light used with texaphyrin is readily transmitted through blood and other endogenous pigments to effect photodynamically-mediated destruction of pigmented and pigment-related tissue as described in U.S. Ser. No. 08/914, 272, issued as U.S. Pat. No. 5,775,339, incorporated by reference herein. PDT requires higher levels of light than for imaging.

The aqueous solubility of texaphyrins is an advantage in the ocular methods of use provided herein, providing for rapid infusion as a bolus as compared to BPD, mTHPC, or SnET2 which require solubilizing vehicles such as lipid environments, for example; and further obviating the need for a lipophilic carrier, use of liposomes, or use of a pump.

The primary excitation (470 nm) and emission peaks (750 nm) for texaphyrin are very widely spaced with a secondary excitation peak available in the infrared range (732 nm) if necessary. Texaphyrins can be administered in a bolus injection, allowing for a sufficiently large amount of drug to be present in the blood and for fast-turnaround between dosing and treatment. Texaphyrins are cleared quickly from the body; no toxicity to the eye has been observed in the use of texaphyrins in the present invention. A further advantage to rapid clearing is that larger vessels clear faster, allowing for imaging and treatment of a neovascular complex. Diagnostic imaging and therapy can be performed with one agent by using texaphyrin as both an angiographic and a PDT agent, thus enabling both accurate determination of dye localization prior to treatment and immediate confirmation of photodynamic closure following treatment.

Following long-standing patent law convention, the terms "a" and "an" mean "one or more" when used in this application, including the claims.

ABBREVIATIONS

ARMD—Age related macular degeneration
BPD—Benzoporphyrin derivative
IN—Inferonasal
IT—Inferotemporal
CNV (M)—Choroidal neovascularization (membrane)
FWHM—full width half maximum
HDL—high-density lipoproteins
ICG—indocynanine green
LDL—Low density lipoprotein
Lu(III)T2BET—lutetium texaphyrin, T2BET
mTHPC—Tetra(m-hydroxyphenyl)chlorin
NZW—New Zealand White
OD—Right eye
OS—Left eye
PDT—Photodynamic therapy
SN—Superonasal
SnET2—Tin etiopurpurin
ST—Superotemporal
TGF-b—Transforming growth factor-b
Txp—Texaphyrin
VEGF—Vascular endothelial growth factor

DETAILED DESCRIPTION OF THE PREFERRED EMBODIMENTS

Figure 1:
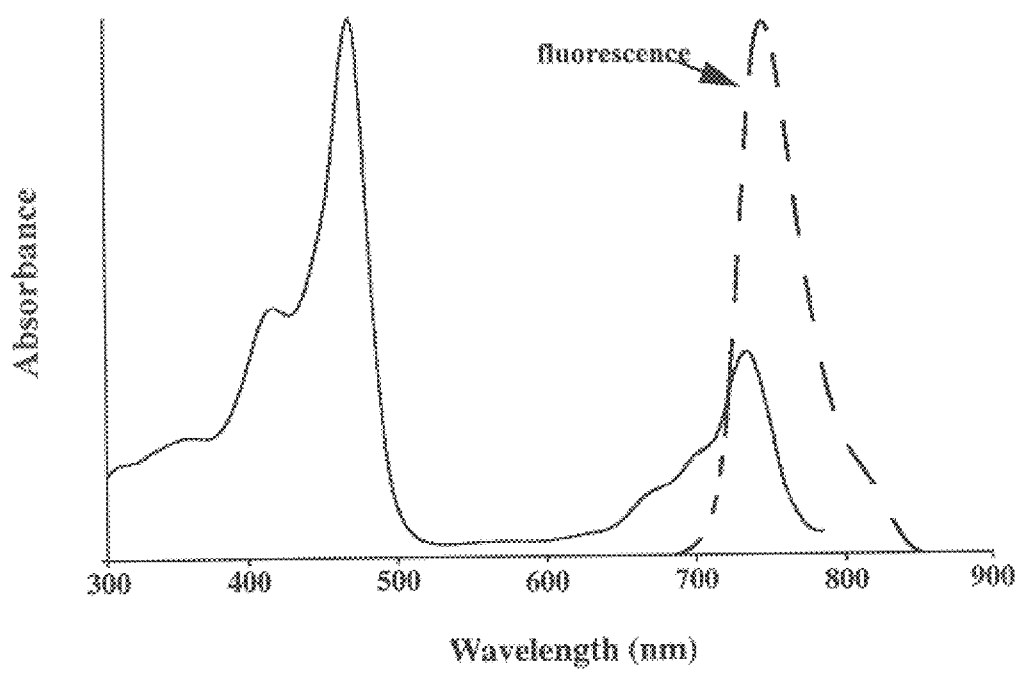
FIG. 1. Absorption spectrum (solid line) and fluorescence profile (broken line) of LuT2BET.

The present invention provides for the use of texaphyrins in the preparation of a pharmaceutical composition for use in ocular diagnosis and therapy; especially diagnostic angiograms, and photodynamic therapy of conditions of the eye characterized by abnormal vasculature. "Abnormal vasculature", as used herein, means undesirable vasculature; neovasculature; irregular, occluded, weeping, or inflamed ocular vessels or ocular tissues; inflammatory ocular membranes; or abnormal conditions having to do with channeling of fluids in the ocular area, especially blood vessels. Conditions having abnormal vasculature include conditions such as macular degeneration, glaucoma, disc or retinal neovascularization in diabetic retinopathy, pannus which is abnormal superficial vascularization of the cornea or conjunctiva, pterygium which is thickening of the bulbar conjunctiva on the cornea, conditions having retinal or choroidal neovasculature, ocular histoplasmosis syndrome, myopia, ocular inflammatory diseases, central serous retinopathy, subretinal neovascular membrane, or neovasculature induced by neoplasm, such as melanoma or retinal blastoma, for example. Treatment of abnormal vasculature related to pigmented and nonpigmented ocular cancers, including melanoma is also contemplated in the use of the present invention. Ocular melanoma includes uveal melanoma, and melanoma of the skin of the eyelids, the conjunctiva, the orbit of the eye, or retinal melanoma.

"Observing the vasculature", as used herein, means carrying out an imaging procedure and collecting information from an angiogram, x-ray, magnetic resonance image, or optical coherence tomogram, for example, to interpret the condition of the eye. The condition of the eye may be normal, or may include vascular leakage or occlusions, for example. As used herein, "eye" or "ocular" includes the eye, underlying and adjacent tissue, and related tissues near and around the eye that have an influence on the functioning of the eye.

The texaphyrin or texaphyrin metal complex for use in ocular diagnosis or photodynamic therapy may have structure I:

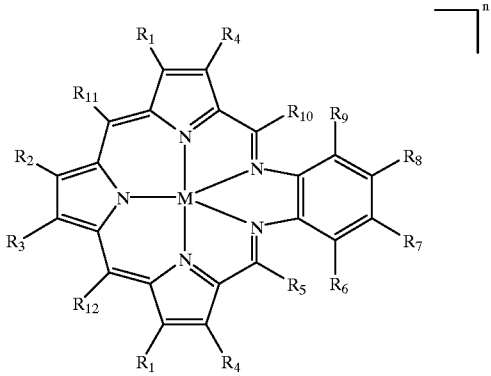

or may have structure II:

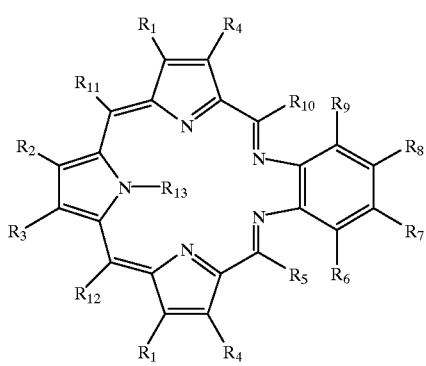

M is a divalent metal cation selected from the group consisting of Ca(II), Mn(II), Co(II), Ni(II), Zn(II), Cd(II), Hg(II), Fe(II), Sm(II), and $UO_2(II)$; or a trivalent metal cation selected from the group consisting of Mn(II), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), and U(III).

$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, aminoalcyl, a site-directing molecule, a catalytic group, or a couple that is coupled to a site-directing molecule or to a catalytic group.

$R_6$ and $R_9$ are independently selected from the groups of $R_1$–$R_4$, $R_7$ and $R_8$, with the proviso that the halide is other than iodide and the haloalkyl is other than iodoalkyl.

$R_5$ and $R_{10}$–$R_{12}$ are independently hydrogen, alkyl, alkenyl, alkynyl, aryl, hydroxyalkyl, alkoxy, hydroxyalkoxy, hydroxyalkenyl, hydroxyalkynyl, carboxyalkyl, carboxyamide, carboxyamidealkyl, amino, aminoalkyl, or a couple that is coupled to a saccharide, to a site-directing molecule, or to a catalytic group; and n is an integer value less than or equal to 5.

$R_{13}$ is alkyl, alkenyl, oxyalkyl, or hydroxyalkyl having up to about 3 carbon atoms and having rotational flexibility around a first-bound carbon atom. Rotational flexibility allows the rest of the group to be positioned outside the plane of the texaphyrin. Thus, for example, a preferred alkenyl is $CH_2$—CH=$CH_2$. The pyrrole nitrogen substituent is most preferably a methyl group.

Fluorescent texaphyrins are used for angiography. The term "fluorescent", as used herein, means that upon photoirradiation by light associated with the absorption profile of texaphyrin, light is emitted at a longer wavelength by the irradiated texaphyrin. All texaphyrins are fluorescent, albeit to varying degrees, and texaphyrins complexed with Y(III), Lu(III), Gd(III), Dy(III), Eu(III), or Mn(III) are preferred as fluorescent texaphyrins, for example. Lutetium texaphyrin, in particular, possesses a strong, broad fluorescence emission profile in the near-infrared centered at 750 mn (FWHM=60 nm) that is not obstructed by endogneous chromophores, thereby exhibiting significant advantages over conventional fluorescein angiography. Further, lutetium texaphyrin exhibits rapid plasma clearance in humans (T1/2α of 0.25 hours), thereby minimizing cutaneous phototoxicity compared to other photosensitizers.

In addition to fluorescent detection, texaphyrins may be imaged by x-radiation, Raman scattering, magnetometry, or by optical coherence tomography; further, texaphyrins complexed with a paramagnetic metal cation may be used for magnetic resonance imaging. Preferred paramagnetic metal cations include Mn(II), Mn(III), Fe(III), or trivalent lanthanide metals other than La(III), Lu(III), and Pm(III). More preferably, the paramagnetic metal is Mn(II), Mn(III), Dy(III), or Gd(III); most preferably, Gd(III). Any of various types of magnetic resonance imaging can be employed in the practice of the invention, including, for example, nuclear magnetic resonance (NMR), NMR spectroscopy, and electronic spin resonance (ESR). The preferred imaging technique is NMR.

Photosensitive texaphyrins are used for photodynamic therapy. A photosensitive texaphyrin may be a free-base texaphyrin or may be metallated with a diamagnetic metal. The term "photosensitive", as used herein, means that upon photoirradiation by light associated with the absorption profile of texaphyrin, texaphyrin effects the generation of oxygen products that are cytotoxic. Cytotoxic oxygen products may be singlet oxygen, hydroxyl radicals, superoxide, hydroperoxyl radicals, or the like. For generating singlet oxygen, the preferred metal is a diamagnetic metal. A preferred diamagnetic metal is Lu(III), La(II), In(III), Zn(II), or Cd(II) and a most preferred diamagnetic metal is Lu(III).

In the above-described structure I, "n" will typically be an integer value less than or equal to 5. In the context of the basic macrocycle with a divalent or trivalent metal cation, n is 1 or 2; however, one skilled in the art in light of the present disclosure would realize that the value of n would be altered due to charges present on substituents $R_1$–$R_{12}$ and charges present on the covalently bound site-directing molecule. It is understood by those skilled in the art that the complexes described in the present invention have one or more additional ligands providing charge neutralization and/or coordinative saturation to the metal ion. Such ligands include chloride, nitrate, acetate, and hydroxide, among others.

Representative examples of alkanes useful as alkyl group substituents of the present invention include methane, ethane, straight-chain, branched or cyclic isomers of propane, butane, pentane, hexane, heptane, octane, nonane and decane, with methane, ethane and propane being preferred. Alkyl groups having up to about thirty, or up to about fifty carbon atoms are contemplated in the present invention. Representative examples of substituted alkyls include alkyls substituted by two or more functional groups as described herein.

Representative examples of alkenes useful as alkenyl group substituents include ethene, straight-chain, branched or cyclic isomers of propene, butene, pentene, hexene, heptene, octene, nonene and decene, with ethene and propene being preferred. Alkenyl groups having up to about thirty or fifty carbon atoms, and up to about five double bonds, or more preferably, up to about three double bonds are contemplated in the present invention.

Representative examples of alkynes useful as alkynyl group substituents include ethyne, straight-chain, branched or cyclic isomers of propyne, butyne, pentyne, hexyne, heptyne, octyne, nonyne and decyne, with ethyne and propyne being preferred. Alkynyl groups having up to about thirty, or up to about fifty carbon atoms, and having up to about five or up to about three triple bonds are contemplated in the present invention.

The aryl may be a compound whose molecules have the ring structure characteristic of benzene, naphthalene, phenanthrene, anthracene, and the like, i.e., either the 6-carbon ring of benzene or the condensed 6-carbon rings of the other aromatic derivatives. For example, an aryl group may be phenyl or naphthyl, unsubstituted or substituted with a nitro, carboxy, sulfonic acid, hydroxy, oxyalkyl or halide substituent. In this case, the substituent on the phenyl or naphthyl may be added in a synthetic step after the condensation step which forms the macrocycle.

Among the halide substituents, chloride, bromide, fluoride and iodide are contemplated in the practice of this invention with the exception of iodide for $R_6$ and $R_9$. $R_6$ and $R_9$ may have chloride, bromide or fluoride substituents. Representative examples of haloalkyls used in this invention include halides of methane, ethane, propane, butane, pentane, hexane, heptane, octane, nonane and decane, with halides, preferably chlorides or bromides, of methane, ethane and propane being preferred.

"Hydroxyalkyl" means alcohols of alkyl groups. Preferred are hydroxyalkyl groups having one to twenty, more preferably one to ten, hydroxyls. "Hydroxyalkyl" is meant to include glycols and polyglycols; diols of alkyls, with diols of $C_{1-10}$ alkyls being preferred, and diols of $C_{1-3}$ alkyls being more preferred; and polyethylene glycol, polypropylene glycol and polybutylene glycol as well as polyalkylene glycols containing combinations of ethylene, propylene and butylene.

Representative examples of oxyalkyls include the alkyl groups as herein described having ether linkages. "Oxyalkyl" is meant to include polyethers with one or more functional groups. The number of repeating oxyalkyls within a substituent may be up to 200, preferably is from 1–20, and more preferably, is 1–10, and most preferably is 1–5. A preferred oxyalkyl is $O(CH_2CH_2O)_xCH_3$ where x=1–100, preferably 1–10, and more preferably, 1–5.

Oxyhydroxyalkyl means alkyl groups having ether or ester linkages, hydroxyl groups, substituted hydroxyl groups, carboxyl groups, substituted carboxyl groups or the like.

Representative examples of thioalkyls include thiols of ethane, thiols of straight-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate-substituted alkyls include alkyls as described above substituted by one or more sulfate groups, a representative example of which is diethyl sulfate (($C_2H_5)_2SO_4$).

Representative examples of phosphates include phosphate or polyphosphate groups. Representative examples of phosphate-substituted alkyls include alkyls as described above substituted by one or more phosphate or polyphosphate groups. Representative examples of phosphonate-substituted alkyls include alkyls as described above substituted by one or more phosphonate groups.

Representative examples of carboxy groups include carboxylic acids of the alkyls described above as well as aryl carboxylic acids such as benzoic acid. Representative examples of carboxyamides include primary carboxyamides ($CONH_2$), secondary ($CONHR'$) and tertiary ($CONR'R''$) carboxyamides where each of R' and R" is a functional group as described herein.

Representative examples of useful amines include a primary, secondary or tertiary amine of an alkyl as described hereinabove.

"Carboxyamidealkyl" means alkyl groups with secondary or tertiary amide linkages or the like. "Carboxyalkyl" means alkyl groups having hydroxyl groups, carboxyl or amide substituted ethers, ester linkages, tertiary amide linkages removed from the ether or the like.

The term "saccharide" includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides, as well as open chain forms of various sugars, and the like. Examples of amine-derivatized sugars are galactosamine, glucosamine, sialic acid and D-glucamine derivatives such as 1-amino-1-deoxysorbitol.

In an embodiment of the present invention, texaphyrins are further coupled to site-directing molecules to form conjugates for targeted in vivo delivery. "Site-directing" means having specificity for targeted sites. "Specificity for targeted sites" means that upon contacting the texaphyrin-conjugate with the targeted site, for example, under physiological conditions of ionic strength, temperature, pH and the like, specific binding will occur. The interaction may occur due to specific electrostatic, hydrophobic, entropic or other interaction of certain residues of the conjugate with specific residues of the target to form a stable complex under conditions effective to promote the interaction. A site-directing molecule may have binding specificity for localization to a treatment site. Exemplary site-directing molecules contemplated in the present invention include, but are not limited to: lipoproteins including low density lipoprotein; cholesterol; polyamides including peptides having affinity for an ocular receptor; proteins such as antibodies or an immunologically active fragment thereof; oligonucleotides complementary to an ocular DNA or RNA; histamine; hormone mimics such as morphine; a catalytic group; and further macrocycles such as sapphyrins and rubyrins. Ocular-specific site-directing molecules may include molecules directed at vascular endothelial growth factor (VEGF), or the class of integrins, both of which are important in ocular angiogenesis. Further site-directing molecules may include b-endorphin, or TGF-b, for example.

The term "catalytic group" means a chemical functional group that assists catalysis by acting as a general acid, Brønsted acid, general base, Brønsted base, nucleophile, or any other means by which the activation barrier to reaction is lowered or the ground state energy of the substrate is increased. Exemplary catalytic groups contemplated include, but are not limited to, imidazole; guanidine; substituted saccharides such as D-glucosamine, D-mannosamine, D-galactosamine, D-glucamine and the like; amino acids such as L-histidine and L-arginine; derivatives of amino acids such as histamine; polymers of amino acids such as poly-L-lysine, $(LysAla)_n$, $(LysLeuAla)_n$ where n is from 1–30 or preferably 1–10 or more preferably 2–7 and the like; derivatives thereof; and texaphyrin metal complexes. The term "appended to the texaphyrin complex-site directing molecule conjugate" means that the catalytic groups are attached either directly to the texaphyrin metal complex or to the texaphyrin complex via a linker or couple of variable length, or are attached to the ligand portion of a texaphyrin complex-ligand conjugate either with or without a linker or couple of variable length.

A preferred site-directing molecule for coupling to texaphyrin is low density lipoprotein (LDL). Human LDL is a physiologic serum protein metabolized by cells via uptake by high affinity receptors. Neovascularization has been shown to have increased numbers of LDL receptors; and by increasing the partitioning of the texaphyrin into the lipoprotein phase of the blood, LDL is expected to more efficiently deliver texaphyrin to the target tissue. A texaphyrin-LDL conjugate is selective for neovascularization since leakage of the conjugate is expected to occur only in neovasculature due to the large size of the conjugate. LDL can be isolated and purified according to the procedure of Hauel et al., (*J. Clin. Invest.*, 34:1345, 1995).

A couple may be described as a linker, i.e., the covalent product formed by reaction of a reactive group designed to attach covalently another molecule at a distance from the texaphyrin macrocycle. Exemplary linkers or couples are amides, arnine, disulfide, thioether, ether, ester, or phosphate covalent bonds.

In most preferred embodiments, conjugates and appended groups are covalently bonded to the texaphyrin via a carbon-carbon, carbon-nitrogen, carbon-sulfur, or a carbon-oxygen bond, more preferably a carbon-oxygen or a carbon-nitrogen bond.

Preferred functionalizations are: when $R_6$ and $R_9$ are other than hydrogen, then $R_5$ and $R_{10}$ are hydrogen or methyl; and when $R_5$ and $R_{10}$ are other than hydrogen, then $R_6$ and $R_9$ are hydrogen, hydroxyl, or halide other than iodide. Other preferred functionalizations are where $R_6$ and $R_9$ are hydrogen, then $R_5$, $R_{10}$, $R_{11}$, and $R_{12}$ are lower alkyl or lower hydroxyalkyl. The lower alkyl is preferably methyl or ethyl, more preferably methyl. The lower hydroxyalkyl is preferably of 1 to 6 carbons and 1 to 4 hydroxy groups, more preferably 3-hydroxypropyl. In a presently preferred embodiment, $R_1$ is $(CH_2)_2CH_2OH$, $R_2$ and $R_3$ are $CH_2CH_3$, $R_4$ is $CH_3$, $R_7$ and $R_8$ a $O(CH_2CH_2O)_2CH_2CH_2OCH_3$, $R_5$, $R_6$, and $R_9$–$R_{12}$ are H, and M is Lu. This texaphyrin is named herein as LuT2BET.

In other presently preferred texaphyrin compounds, $R_1$–$R_{12}$ are as in Tables A and B for texaphyrins A1–A108, and M is as defined hereinabove. However, while the above-described texaphyrins are presently preferred compounds for use in the present invention, the invention is not limited thereto and any photosensitive texaphyrin may be useful for PDT, and any fluorescent texaphyrin may be useful for angiography.

TABLE A

Representative Substituents for Texaphyrin Macrocycles A1–A108 of the Present Invention. Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A1 | $CH_2(CH_2)_2OH$ | $CH_2CH_3$ | $CH_2CH_3$ | $CH_3$ | H | H |
| A2 | " | " | " | " | " | " |
| A3 | " | " | " | " | " | " |
| A4 | " | " | " | " | " | " |
| A5 | " | " | " | " | " | " |
| A6 | " | " | " | " | " | " |
| A7 | " | " | " | " | " | " |
| A8 | " | " | " | " | " | " |
| A9 | " | " | " | " | " | " |
| A10 | " | " | " | " | " | " |
| A11 | " | " | " | " | " | " |
| A12 | " | COOH | COOH | " | " | " |
| A13 | $CH_2(CH_2)_2OH$ | $COOCH_2CH_3$ | $COOCH_2CH_3$ | $CH_3$ | H | H |
| A14 | $CH_2CH_2CON(CH_2CH_2OH)_2$ | $CH_2CH_3$ | $CH_2CH_3$ | " | " | " |
| A15 | $CH_2CH_2ON(CH_3)CH_2$—$(CHOH)_4CH_2OH$ | " | " | " | " | " |
| A16 | $CH_2CH_3$ | " | " | " | " | " |
| A17 | $CH_2(CH_2)_2OH$ | " | " | " | " | " |
| A18 | " | " | " | " | " | " |
| A19 | " | " | " | " | " | " |
| A20 | $CH_2CH_3$ | $CH_3$ | $CH_2CH_2COOH$ | " | " | " |
| A21 | " | " | $CH_2CH_2CO$-VEGF | " | " | " |
| A22 | $CH_2(CH_2)_2OH$ | $CH_2CH_3$ | $CH_2CH_3$ | " | " | " |
| A23 | " | " | " | " | " | " |
| A24 | " | " | " | " | " | " |
| A25 | " | " | " | " | " | " |
| A26 | " | " | " | " | " | " |
| A27 | " | COOH | COOH | " | " | " |
| A28 | " | $COOCH_2CH_3$ | $COOCH_2CH_3$ | " | " | " |
| A29 | $CH_2CH_2CO$-VEGF | $CH_2CH_3$ | $CH_2CH_3$ | $CH_3$ | H | H |
| A30 | $CH_2CH_2O$-VEGF | " | " | " | " | " |
| A31 | $CH_2(CH_2)_2OH$ | " | $CH_2CH_2CO$-VEGF | " | " | " |
| A32 | " | " | " | " | " | " |
| A33 | $CH_2CH_3$ | $CH_3$ | $CH_2CH_2COOH$ | " | " | " |
| A34 | " | " | $CH_2CH_2CO$-VEGF | " | " | " |
| A35 | $CH_2CH_3$ | $CH_2CH_3$ | $CH_2CH_3$ | " | " | " |

TABLE A-continued

Representative Substituents for Texaphyrin Macrocycles A1–A108 of the Present Invention.
Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A36 | " | " | " | " | " | " |
| A37 | " | " | " | " | " | " |
| A38 | " | " | " | " | " | " |
| A39 | $CH_2(CH_2)_2OH$ | $CH_2CH_3$ | $CH_2CH_3$ | $CH_3$ | H | COOH |
| A40 | " | " | " | " | " | COOH |
| A41 | " | " | " | " | " | CONHCH—$(CH_2OH)_2$ |
| A42 | " | " | " | " | " | " |
| A43 | " | " | " | " | " | H |
| A44 | " | " | " | " | " | $OCH_3$ |
| A45 | " | " | " | " | " | " |
| A46 | " | " | " | " | " | " |
| A47 | " | " | " | " | " | " |
| A48 | " | " | " | " | " | " |
| A49 | " | " | " | " | " | " |
| A50 | " | " | " | " | " | " |
| A51 | " | " | " | " | " | " |
| A52 | " | " | " | " | " | " |
| A53 | " | " | " | " | " | " |
| A54 | " | " | " | " | $CH_3$ | H |
| A55 | " | " | " | " | " | " |
| A56 | " | " | " | " | " | " |
| A57 | $CH_2(CH_2)_2OH$ | $CH_2CH_3$ | $CH_2CH_3$ | $CH_3$ | $CH_3$ | H |
| A58 | " | " | " | " | " | " |
| A59 | " | " | " | " | " | " |
| A60 | " | " | " | " | " | " |
| A61 | " | " | " | " | " | " |
| A62 | " | " | " | " | " | " |
| A63 | " | " | " | " | " | OH |
| A64 | " | " | " | " | " | F |
| A65 | " | " | " | " | $CH_2(CH_2)_6OH$ | H |
| A66 | " | " | " | " | H | Br |
| A67 | " | " | " | " | " | $NO_2$ |
| A68 | " | " | " | " | " | COOH |
| A69 | " | " | " | " | " | $CH_3$ |
| A70 | " | " | " | " | $C_6H_5$ | H |
| A71 | " | COOH | COOH | " | $CH_2CH_3$ | " |
| A72 | " | $COOCH_2CH_3$ | $COOCH_2CH_3$ | " | $CH_3$ | " |
| A73 | $CH_2CH_2CON(CH_2CH_2OH)_2$ | $CH_2CH_3$ | $CH_2CH_3$ | " | " | " |
| A74 | $CH_2CH_2ON(CH_3)CH_2(CHOH)_4CH_2OH$ | " | " | " | " | " |
| A75 | $CH_2CH_3$ | " | " | " | $CH_2(CH_2)_6OH$ | " |
| A76 | $CH_2(CH_2)_2OH$ | $CH_2CH_3$ | $CH_2CH_3$ | $CH_3$ | $CH_3$ or $CH_2CH_3$ | H |
| A77 | " | " | " | " | " | " |
| A78 | " | " | " | " | " | " |
| A79 | " | " | " | " | " | " |
| A80 | " | " | " | " | " | " |
| A81 | " | " | " | " | " | " |
| A82 | " | " | " | " | " | " |
| A83 | " | " | " | " | " | " |
| A84 | " | " | " | " | " | " |
| A85 | " | " | " | " | H | " |
| A86 | " | " | " | " | " | " |
| A87 | " | " | " | " | $CH_3$ or $CH_2CH_3$ | " |
| A88 | " | " | " | " | " | " |
| A89 | " | " | " | " | H | H |
| A90 | " | " | " | " | " | " |
| A91 | " | " | " | " | " | " |
| A92 | " | " | " | " | " | " |
| A93 | " | COOH | COOH | " | " | " |
| A94 | " | COOCH2CH3 | COOCH2CH3 | | | |
| A95 | CH2(CH2)2OH | CH2CH3 | CH2CH2CO-VEGF | | | |
| A96 | CH2CH3 | CH3 | CH2CH2COOH | " | " | " |
| A97 | " | " | CH2CH2CO-VEGF | " | " | " |
| A98 | CH2CH3 | " | " | " | " | " |
| A99 | " | " | " | " | " | " |
| A100 | " | " | " | " | " | " |
| A101 | " | " | " | " | " | " |
| A102 | " | " | " | " | " | " |
| A103 | " | " | " | " | " | " |
| A104 | " | " | " | " | " | " |
| A105 | $CH_2(CH_2)_2OH$ | " | " | " | " | " |

TABLE A-continued

Representative Substituents for Texaphyrin Macrocycles A1–A108 of the Present Invention.
Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A106 | " | " | " | " | " | " |
| A107 | " | " | " | " | " | " |
| A108 | " | " | " | " | " | " |

TABLE B

Representative Substituents for Texaphyrin Macrocycles A1–A108 of the Present Invention.
Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A1 | $O(CH_2)_3OH$ | $O(CH_2)_3OH$ | H | H | H | H |
| A2 | $O(CH_2CH_2O)_3CH_3$ | $O(CH_2CH_2O)_3CH_3$ | " | " | " | " |
| A3 | O(CHACON-linker-VEGF, n = 1–10 | " | " | " | " | " |
| A4 | O(CHACON-linker-VEGF, n = 1–10 | H | " | " | " | " |
| A5 | $OCH_2CO$-VEGF | " | " | " | " | " |
| A6 | $O(CH_2CH_2O)_3CH_3$ | " | " | " | " | " |
| A7 | $OCH_2CON$-linker-VEGF | $O(CH_2CH_2O)_3CH_3$ | " | " | " | " |
| A8 | $OCH_2CO$-VEGF | " | " | " | " | " |
| A9 | $O(CH_2CH_2O)_{100}CH_3$ | " | " | " | " | " |
| A10 | $OCH_2CON(CH_2CH_2OH)_2$ | H | " | " | " | " |
| A11 | $CH_2CON(CH_3)CH_2$-$(CHOH)_4CH_2OH$ | " | " | " | " | " |
| A12 | " | " | " | " | " | " |
| A13 | $CH_2CON(CH_3)CH_2$-$(CHOH)_4CH_2OH$ | H | H | H | H | H |
| A14 | " | " | " | " | " | " |
| A15 | $OCH_3$ | $OCH_3$ | " | " | " | " |
| A16 | $OCH_2CO_2$-VEGF | H | " | " | " | " |
| A17 | $O(CH_2)_nCOOH$, n = 1–10 | " | " | " | " | " |
| A18 | $(CH_2)_n$-CON-linker-VEGF, n = 1–10 | " | " | " | " | " |
| A19 | $YCOCH_2$-linker-VEGF, Y = NH,O | " | " | " | " | " |
| A20 | $O(CH_2)_2CH_2OH$ | $O(CH_2)2CH_2OH$ | " | " | " | " |
| A21 | " | " | " | " | " | " |
| A22 | $OCH_2COOH$ | $O(CH_2CH_2O)_3CH_3$ | " | " | " | " |
| A23 | $O(CH_2)_nCO$-VEGF, n = 1–10 | H | " | " | " | " |
| A24 | $O(CH_2CH_2O)_3CH_3$ | $O(CH_2CH_2O)_3$-linker-VEGF, n = 1–10 | " | " | " | " |
| A25 | $OCH_3$ | $OCH_2CO$-VEGF | " | " | " | " |
| A26 | " | $CH_2CO$-VEGF | " | " | " | " |
| A27 | " | " | " | " | " | " |
| A28 | $OCH_3$ | $CH_2CO$-VEGF | H | H | H | H |
| A29 | " | $OCH_3$ | " | " | " | " |
| A30 | " | " | " | " | " | " |
| A31 | H | $O(CH_2)_nCOOH$, n = 1–10 | " | " | " | " |
| A32 | " | $(CH_2)_n$-CON-linker-VEGF, n = 1–10 | " | " | " | " |
| A33 | $OCH_3$ | $O(CH_2CH_2O)_3$—$CH_3$ | " | " | " | " |
| A34 | " | " | " | " | " | " |
| A35 | H | $O(CH_2)_nCO$-VEGF, n = 1–10 | " | " | " | " |
| A36 | $OCH_3$ | " | " | " | " | " |
| A37 | $O(CH_2CH_2O)_3CH_3$ | " | " | " | " | " |
| A38 | " | $O(CH_2CH_2O)_N$-VEGF, n = 1–10 | " | " | " | " |
| A39 | $O(CH_2)_3OH$ | $O(CH_2)_3OH$ | $O(CH_2)_3OH$ | H | H | H |
| A40 | $O(CH_2CH_2O)_3CH_3$ | $O(CH_2CH_2O)_3CH_3$ | COOH | " | " | " |
| A41 | $O(CH_2CH_2O)_3CH_3$ | $O(CH_2CH_2O)_3CH_3$ | $(CH_2)_3OH$ | " | " | " |
| A42 | " | " | $O(CH_2CH_2O)_3CH_3$ | " | " | " |
| A43 | " | $O(CH_2)_3COOH$ | " | " | " | " |
| A44 | H | $OCH_2COOH$ | $OCH_3$ | " | " | " |
| A45 | " | $OCH_2COOH$ | " | " | " | " |
| A46 | " | $O(CH_2CH_2O)_3CH_3$ | " | " | " | " |
| A47 | $O(CH_2CH_2O)_3CH_3$ | " | " | " | " | " |
| A48 | " | $OCH_2CO$-VEGF | " | " | " | " |
| A49 | " | $OCH_2COOH$ | " | " | " | " |
| A50 | " | $O(CH_2CH_2O)_3CH_3$ | $O(CH_2CH_2O)_3CH_3$ | " | " | " |
| A51 | " | $OCH_2COOH$ | " | " | " | " |
| A52 | $O(CH_2CH_2O)_3CH_3$ | $O(CH_2CH_2O)_{100}CH_3$ | $OCH_3$ | " | " | " |
| A53 | H | $OCH_2CO$-VEGF | " | " | " | " |

TABLE B-continued

Representative Substituents for Texaphyrin Macrocycles A1–A108 of the Present Invention.
Substituents for R$_1$–R$_6$ are provided in TABLE A and for R$_7$–R$_{12}$ in TABLE B.

| TXP | R$_1$ | R$_2$ | R$_3$ | R$_4$ | R$_5$ | R$_6$ |
|---|---|---|---|---|---|---|
| A54 | O(CH$_2$)$_3$OH | O(CH$_2$)$_3$OH | H | CH$_3$ | " | " |
| A55 | H | O(CH$_2$CH$_2$O)$_3$CH$_3$ | " | " | " | " |
| A56 | O(CH$_2$CH$_2$O)$_3$CH$_3$ | " | " | " | " | " |
| A57 | H | OCH$_2$CO-VEGF | H | CH$_3$ | " | " |
| A58 | " | OCH$_2$CO-VEGF | " | " | " | " |
| A59 | " | OCH$_2$CON(CH$_2$CH$_2$OH)$_2$ | " | " | " | " |
| A60 | O(CH$_2$CH$_2$O)$_3$CH$_3$ | O(CH$_2$CH$_2$O)$_{100}$CH$_3$ | " | " | " | " |
| A61 | " | OCH$_2$CO-VEGF | " | " | " | " |
| A62 | H | CH$_2$CON(CH$_3$)CH$_2$(CHOH)$_4$CH$_2$OH | " | " | " | " |
| A63 | O(CH$_2$CH$_2$O)$_3$CH$_3$ | O(CH$_2$CH$_2$O)$_3$CH$_3$ | OH | " | " | " |
| A64 | " | " | F | " | " | " |
| A65 | " | " | H | CH$_2$(CH$_2$)$_6$OH | " | " |
| A66 | " | " | Br | H | " | " |
| A67 | " | " | NO$_2$ | " | " | " |
| A68 | " | " | COOH | " | " | " |
| A69 | " | " | CH$_3$ | " | " | " |
| A70 | " | " | H | C$_6$H$_5$ | " | " |
| A71 | " | " | " | CH$_2$CH$_3$ | " | " |
| A72 | " | " | " | CH$_3$ | " | " |
| A73 | " | " | " | " | " | " |
| A74 | OCH$_3$ | OCH$_3$ | " | " | " | " |
| A75 | H | OCH$_2$CO-VEGF | " | CH$_2$(CH$_2$)$_6$OH | " | " |
| A76 | O(CH$_2$)$_3$OH | O(CH$_2$)$_3$OH | H | CH$_3$ or CH$_2$CH$_3$ | CH$_3$ or CH$_2$CH$_3$ | CH$_3$ or CH$_2$CH$_3$ |
| A77 | O(CH$_2$CH$_2$O)$_3$CH$_3$ | O(CH$_2$CH$_2$O)$_3$CH$_3$ | " | " | " | " |
| A78 | O(CH$_2$)$_3$OH | O(CH$_2$CH$_2$O)$_3$CH$_3$ | " | " | " | " |
| A79 | H | O(CH$_2$)$_n$CO-VEGF, n = 1,2,3 | " | " | " | " |
| A80 | H | O(CH$_2$)$_3$CO-VEGF, n = 1,2,3 | " | " | " | " |
| A81 | H | O(CH$_2$)$_3$OH | " | " | " | " |
| A82 | O(CH$_2$)$_3$OH | O(CH$_2$)$_n$CO-VEGF, n = 1,2,3, | " | " | " | " |
| A83 | O(CH$_2$CH$_2$O)$_3$CH$_3$ | O(CH$_2$)$_n$CO-VEGF, n = 1–10 | " | " | " | " |
| A84 | " | O(CH$_2$)$_n$CO-VEGF, n = 1,2,3 | " | " | " | " |
| A85 | " | O(CH$_2$CH$_2$O)$_3$CH$_3$ | " | " | " | " |
| A86 | " | " | " | " | CH$_2$(CH$_2$)$_2$OH | CH$_2$(CH$_2$)$_2$OH |
| A87 | " | " | " | CH$_3$ or CH$_2$CH$_3$ | " | " |
| A88 | " | O(CH$_2$CH$_2$O)$_3$CH$_3$ | " | " | " | " |
| A89 | O(CH$_2$CH$_2$O)$_3$CH$_2$—CH$_2$— | O(CH$_2$CH$_2$O)$_{120}$CH$_3$-VEGF | " | " | " | " |
| A90 | H | VEGF | " | " | " | " |
| A91 | OCH$_2$CO-VEGF | OCH$_2$CO-VEGF | " | " | " | " |
| A92 | CH$_2$CO-VEGF | CH$_2$CO-VEGF | " | " | " | " |
| A93 | " | " | " | " | " | " |
| A94 | " | " | " | " | " | " |
| A95 | H | YCOCH$_2$-linker-VEGF Y=NH,O | " | " | " | " |
| A96 | O(CH$_2$CH$_2$O)$_3$CH$_3$ | O(CH$_2$CH$_2$O)$_5$-VEGF | " | " | " | " |
| A97 | " | " | " | " | " | " |
| A98 | H | O(CH$_2$)$_3$CO-VEGF | " | " | " | " |
| A99 | " | " | " | " | " | " |
| A100 | OCH$_3$ | " | " | " | " | " |
| A101 | O(CH$_2$CH$_2$O)$_3$CH$_3$ | " | " | " | " | " |
| A102 | — | O(CH$_2$CH$_2$O)$_n$-VEGF, n = 1–10 | " | " | " | " |
| A103 | " | O(CH$_2$CH$_2$O)$_n$-VEGF, n = 6 | " | " | " | " |
| A104 | " | O(CH$_2$CH$_2$O)$_n$-VEGF, n = 3 | " | " | " | " |
| A105 | " | " | " | " | " | " |
| A106 | OCH$_3$ | O(CH$_2$CH$_2$O)$_n$VEGF n = 1–10 | " | " | " | " |
| A107 | H | " | " | " | " | " |
| A108 | O(CH$_2$CH$_2$O)$_n$CH$_3$, x = 1–10 | " | " | " | " | " |

Importantly, texaphyrins may be synthesized using certain substituents to effect a lipid-water distribution coefficient that is optimal for use in the eye, i.e., sufficiently water soluble for uptake into vascular tissues and for ease of handling. "Water soluble" means soluble in aqueous fluids to about 1 mM or better. U.S. Patents, PCT publications, and pending applications to texaphyrins, methods of making and uses thereof have been listed herein and incorporated by reference herein. Sapphyrin compounds are disclosed in U.S. Pat. Nos. 5,041,078; 5,159,065; 5,120,411; 5,302,714; and 5,457,195; each patent is incorporated by reference herein.

One skilled in the art of organic synthesis in light of the present disclosure and the disclosures in the patents, applications and publications incorporated by reference herein could extend and refme the referenced basic synthetic chemistry to produce texaphyrins having various substituents. For example, polyether-linked polyhydroxylated groups, saccharide substitutions in which the saccharide is appended via an acetal-like glycosidic linkage, an oligosaccharide or a polysaccharide may be similarly linked to a texaphyrin. A doubly carboxylated texaphyrin in which the carboxyl groups are linked to the texaphyrin core via aryl ethers or functionalized alkyl substituents could be converted to various esterified products wherein the ester linkages serve to append further hydroxyl-containing substituents. Polyhydroxylated texaphyrin derivatives may be synthesized via the use of secondary amide linkages. Saccharide moieties may be appended via amide bonds. Polyhydroxylated texaphyrin derivatives containing branched polyhydroxyl (polyol) subunits may be appended to the texaphyrin core via aryl ethers or ester linkages.

Treatment of carboxylated texaphyrins with thionyl chloride orp-nitrophenol acetate would generate activated acyl species suitable for attachment to monoclonal antibodies or other biomolecules of interest. Standard in situ coupling methods (e.g., 1,1'-carbonyldiimidazole) could be used to effect the conjugation.

For the above-described uses, texaphyrins are provided as pharmaceutical preparations. A pharmaceutical preparation of a texaphyrin may be administered alone or in combination with pharmaceutically acceptable carriers, in either single bolus or multiple doses. Preferable pharmaceutical carriers include sterile aqueous solutions. The pharmaceutical compositions formed by combining a texaphyrin of the present invention and the pharmaceutically acceptable carriers are then easily administered in a variety of dosage forms. Administration may be intravenous, intramuscular, subcutaneous, ophthalmic, retrobulbar, juxtabulbar, or topical, with intravenous, topical, ophthalmic, or retrobulbar administration being preferred, and intravenous being more preferred.

Solutions of the texaphyrin in aqueous propylene glycol or in sterile aqueous solution may be employed. Such aqueous solutions should be suitably buffered if necessary and the liquid diluent first rendered isotonic with sufficient saline or glucose. In this connection, sterile aqueous media which can be employed will be known to those of skill in the art in light of the present disclosure. Topical creams, emulsions, solutions, and the like are contemplated for applications to surface areas of the ocular area.

Pharmaceutical forms include sterile aqueous solutions or dispersions and sterile powders for the extemporaneous preparation of sterile injectable solutions or dispersions. Preferably, the form is sterile, fluid to the extent that easy use with a syringe exists, stable under the conditions of manufacture and storage, and is preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. A more preferable isotonic agent is a mannitol solution of about 2–8% concentration, and, most preferably, of about 5% concentration. Prolonged absorption of the injectable compositions can be brought about by the use in the compositions of agents delaying absorption, for example, aluminum monostearate and gelatin.

Sterile solutions are prepared by incorporating the texaphyrin in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, permeation enhancers, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The texaphyrin to be used in the angiographic or photodynamic methods of the invention will be administered in a pharmaceutically effective amount. By "pharmaceutically effective" is meant a dose that will provide an image for angiography or, upon exposure to light of the appropriate wavelength, provide substantial treatment of abnormal vasculature. The specific dose will vary depending on the particular texaphyrin chosen, the dosing regimen to be followed, photoirradiation exposure, timing of administration, the tissue or disease to be treated, the sensitivity of the detector, the filters used for visualization, and the physical delivery system in which it is carried. Such dose can be determined without undue experimentation by methods known in the art or as described herein.

The parameters used for effective angiography and effective treatment in the invention are interrelated. Therefore, the dose is adjusted with respect to other parameters, for example, fluence, irradiance, duration of the light used in photodynamic therapy, and the time interval between administration of the dose and the therapeutic irradiation. Such parameters should be adjusted to produce significant damage to abnormal vascular tissue without significant damage to the surrounding tissue or, on the other hand, to enable the observation of blood vessels in the eye without significant damage to the surrounding tissue. Typically, the dose of texaphyrin used is within the range of from about 0.001 $\mu$mol/kg to about 15 $\mu$mol/kg/treatment, and preferably from about 0.01–5 $\mu$mol/kg/treatment. The lower dosage limit is dependent upon the detection system used and, as methods of detection improve, may be decreased. Further, as the texaphyrin dose is reduced, the fluence required to treat neovascular tissue may change.

After the photosensitizing texaphyrin has been administered, the tissue being treated in the eye is irradiated at a wavelength similar to the absorbance of the texaphyrin, usually either about 400–500 nm or about 700–800 nm. In the present photodynamic therapy methods, the light source may be a laser, a light-emitting diode, or filtered light from, for example, a xenon lamp; the light may have a wavelength range of about 400–900 nm, preferably about 400–500 nm or 700–800 nm, more preferably about 450–500 nm or about 710–760 nm, or most preferably about 450–500 nm or about 725–740 nm; and the light may be administered topically, endoscopically, or interstitially (via, e.g., a fiber optic probe). Preferably, the light is administered using a slit-lamp delivery system. A wavelength in this range is especially preferred since blood and retinal pigment epithelium (RPE) are relatively transparent at longer wavelengths and, therefore, treatment results in less tissue damage and better light penetration. The fluence and irradiance during the irradiating treatment can vary depending on type of tissue, depth of target tissue, and the amount of overlying fluid or blood.

As a result of being irradiated, the texaphyrin in its triplet state is thought to interact with oxygen and other compounds to form reactive intermediates, such as singlet oxygen, which can cause disruption of cellular structures. Possible cellular targets include the cell membrane, mitochondria, lysosomal membranes, melanosome, endoplasmic reticulum, the Golgi apparatus, and the nucleus. Occlusion of the vasculature is thought to be a major mechanism of photodynamic therapy which occurs by damage to endothelial cells with subsequent platelet adhesion, degranulation, and thrombus formation.

The optimum length of time following texaphyrin administration until light treatment can vary depending on the mode of administration, the form of administration, and the type of target tissue. For example, a time interval of seconds to about 5 h should be appropriate for vasculature in the eye. The time of light irradiation after administration of the texaphyrin may be important as one way of maximizing the selectivity of the treatment, thus minimizing damage to structures other than the target tissues. For a human, it is believed that the texaphyrin begins to reach the retinal and choroidal vasculature within seconds following administration. Typically, the texaphyrin persists for a period of minutes to hours, depending on the texaphyrin, the formulation, the dose, the infusion rate, as well as the type of vessel and vessel size.

In addition, texaphyrin can be used to observe the condition of blood vessels as a single agent, or in concert with other dyes such as fluorescein or indocyanine green to follow the progress of destruction of abnormal vascular tissue. In an angiographic system, a sufficient amount of texaphyrin is administered to produce an observable fluorescent emission when excited by light, preferably light having a wavelength range of about 400–900 nm, preferably about 400–500 nm or 700–800 nm, more preferably about 450–500 nm or about 710–760 nm, or most preferably about 450–500 nm or about 725–740 nm. Images are recorded by illuminating the eye with light in the excitation wavelength range and detecting the amount of fluorescent light emitted at the emission wavelength of about 700–800 nm, preferably about 730–760 nm. One such device, which both emits and receives light in the 430–760 nm range, is the TOPCON™ 50VT camera in the Ophthalmic Imaging System (Ophthalmic Imaging System Inc., 221 Lathrop Way, Suite 1, Sacramento Calif.). Generally, visualization is with a laser scanning microscope, and the activating wavelength for fluorescence detection is that of the laser. Imaging using wavelengths of light in the near-infrared range eliminates autofluorescence and enables efficient light penetration through tissue, particularly hemorrhagic and pigmented tissue.

A camera is used to collect the emitted fluorescent light, digitize the data, and store it for later depiction on a video screen, as a hard paper copy, or in connection with some other imaging system. While a film-recording device may be used when additional dyes such as fluorescein are being used in combination with the texaphyrin, a CCD camera (charge-coupled device) is preferable as being able to capture emissions at higher wavelengths. As a result, one can obtain more sophisticated information regarding the pattern and extent of vascular structures in different ocular tissue layers, giving the ability to detect the "leakiness" that is characteristic of new or inflamed blood vessels. Further, it is preferable to use a camera that is capable of providing the excitation light, appropriately filtered to deliver only light of the desired excitation wavelength range, and then to capture the emitted, fluorescent light with a receiving device, appropriately filtered to receive only light in the desired emission wavelength range.

The following example is included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE

Texaphyrins for Angiography and for
Photodynamic Therapy of Vascular Lesions of the
Eye The present example provides results from studies using Lu(III)T2BET, cited herein, for fluorescent digital angiography of the eye and for photodynamic therapy of vascular lesions of the eye. LuT2BET has broad absorption bands at 470 and 732 nm ($\epsilon$=32,000 $M^{-1}cm^{-1}$ at 732 nm), is highly fluorescent, and exhibits an intense emission profile centered at 750 nm as shown in FIG. 1. The wavelength range from 700–800 nm is diagnostically important since autofluorescence from endogneous chromophores (<700 nm) does not hinder the emission signal.

Fluorescence angiography comparing LuT2BET, fluorescein, and ICG was performed on normal NZW rabbits. Normal rabbits (n=4) received an intravenous injection of LuT2BET from 1–10 $\mu$mol/kg after intramuscular sedation and pupillary dilatation. Extensive fundoscopy was performed immediately and up to 2 hours post texaphyrin, fluorescein, or ICG administration. Fluorescein and ICG angiography, in addition to H&E histology, revealed no evidence of normal tissue damage, demonstrating that lutetium texaphyrin fluorescence angiography appears safe. In further studies, vascular lesions including neovascularization was induced in albino rabbits (NZW) using photocoagulation. PDT using LuT2BET was carried out on the induced lesions. The results demonstrate that vascular occlusions, areas of decreased perfusion, and areas of neovascularization can be identified, showing that texaphyrin is an effective agent for fluorescent angiography. The results also demonstrate closure of induced vascular lesions using PDT with texaphyrin, showing that texaphyrin is an effective agent for PDT of abnormal vasculature of the eye. Therefore, selective accumulation of Lu(III)T2BET in areas of neovascularization should facilitate diagnosis and photodynamic therapy of age-related macular degeneration and other disorders related to abnormal vasculature.

Dyes. Lutetium texaphyrin, Lu(III)T2BET, was dissolved in 5% mannitol at a concentration of 2 mM. Indocyaninegreen (ICG, Cardio-Gree"®, Becton Dickinson and Company, Cockeysville, Md.) and fluorescein (Alcon Laboratories, Fort Worth, Tex.) fluorescent angiograms were performed at concentrations of 0.31 mg/kg and 7.5 mg/kg, respectively. All administrations were performed via the ear vein.

Animals. Studies were designed and performed in accordance with the Association for Research in Vision and Ophthalmology (ARVO) resolution on the use of animals in research. Male New Zealand White rabbits, weighing 3 to 4 kg, were obtained from R&R Rabbitry (Stanwood, Wash.). Rabbits received regular Purina Laboratory Rabbit Chow and water ad libidum for the entire duration of the study. Each rabbit studied was anesthetized with a Ketamine (8.4 mg/kg)/Rompun (1.2 mg/kg) cocktail administered via the ear vein. Pupils were dilated with tropicamide (MYDRIACYL®1%, Alcon Laboratories, Fort Worth, Tex.) and 0.5% proparacaine (ALCAINE®, Alcon Laboratories, Fort Worth, Tex.), 10% phenylephrine (AK-DILATE®, Akom, Inc., Abita Springs, La.) was used for topical anesthesia. No measures were taken to protect the animals from ambient light.

Photography. Fundus photography and fluorescence angiograms were performed with the TOPCON™ 50VT camera coupled to the Ophthalmic Imaging System (Ophthalmic Imaging System Inc., Sacramento, Calif.). Lu-Tex imaging was performed with conventional excitation and interference filters. ICG was excited at 790–805 nm and fluorescence detected at 835 nm. Fluorescein protocol included excitation at 465–490 nm, with emission at 520–530 nm. A xenon lamp was used to activate the dyes.

Induction ofNeovascularization. Photocoagulation burns were introduced in the right macular retina of seven rabbits with an argon dye laser (Coherent Inc., Palo Alto, Calif.). On average, five lesions were induced with 577 nm light using a spot size of 50 $\mu$m using enough power (typically 450 mW) to cause bleeding into the retina. The eyes were photographed immediately after photocoagulation. Fluorescein and ICG angiograms were performed 11–15 days after photocoagulation. Neovascular lesions exhibited hyperfluorescence immediately after injection followed by leakage. Two animals had a grid of ten lesions induced in the medullary ray (200 $\mu$m spot size for 0.2 seconds using a set power of 300 mW). Four control animals, having no induced lesions, were given fluorescence angiograms with the respective dyes.

PDT Protocol. Animals received Lu(III)T2BET, 30 minutes post injection laser light at 488 nm, spot size of 1000 $\mu$m, was directed to each lesion via a slitlamp system. Fluorescein angiography was performed throughout the procedure, from prior to until after PDT.

Plasma Analysis. Rabbits were injected via the ear vein with 1 $\mu$mol Lu(III)T2BET/kg and blood was collected at 15 min, 30 min, 3 hr, and 5 hr post administration. EDTA was used as the anticoagulant. Plasma samples (25 $\mu$l) were mixed with 10 mM Triton X100 (3 ml) and analyzed by fluorescence. Fluorescence spectra were acquired with a SLM 48000S instrument, excitation was between 450–480 nm and emission monitored from 700–800 nm. In vivo binding of Lu(III)T2BET to rabbit plasma proteins and lipoproteins was assessed using KBr density-gradient ultracentrifugation to fractionate the protein/lipoprotein mixture, followed by fluorescence spectroscopy to determine the relative distribution of Lu(III)T2BET among the low-density lipoproteins (LDL), high-density lipoproteins (HDL), and heavy proteins.

Histologic Evaluation. Eyes were enucleated under deep anesthesia and fixed in 10% buffered formalin. The rabbits were then sacrificed with an overdose of pentobarbital (100 mg/kg). Tissues were embedded in paraffin and sequential sections, taken every 5 mm to the center of the eye, were stained with hematoxylin and eosin (H&E) for light microscopic evaluation.

Figure 2:
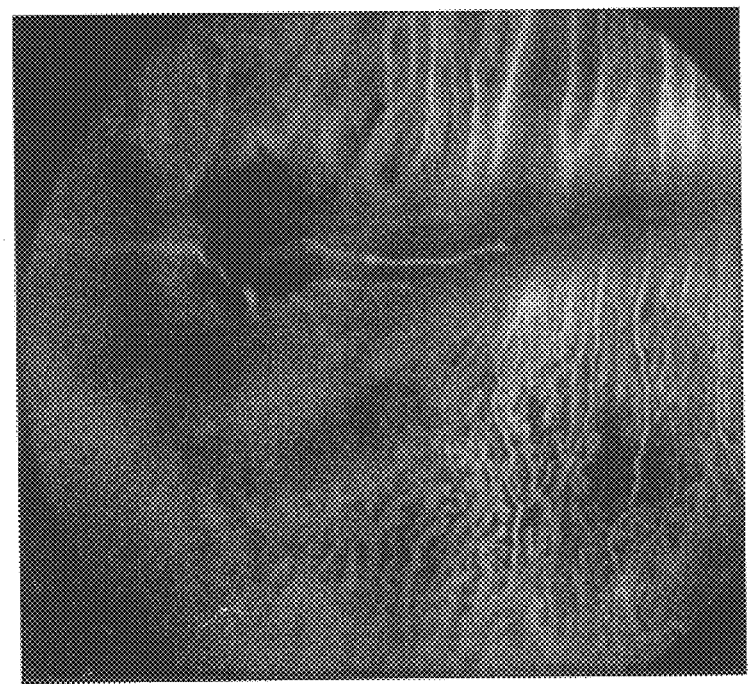
FIG. 2. LuT2BET fluorescent angiogram of the eye of an NZW rabbit in which a lesion (laser coagulation) in the inferior nasal quadrant had been produced a few weeks prior to the angiogram. The image was obtained immediately after injection of 4 μmol LuT2BET/kg injection and reveals the retinal vessels emanating from the optic disc, which is the dark area, at 9:00 o'clock to the left of the center of the eye. The vessels crossing horizontally represent the branches of the ophthalmic artery and vessels running vertically represent the arteries and veins in the choroid. An acute lesion (occlusion) has also been placed in one of the main arteries emanating from the optic disc (seen better in the late phase angiogram, FIG. 3). The round hypovascular area at 4:00 and 5:00 o'clock at the edge of the visualized portion of the retina is the area where the previous thermal ablation occurred.

FIG. 2 provides a LuT2BET angiogram of the right eye of an NZW rabbit immediately following a 4 $\mu$mol/kg injection of lutetium texaphyrin. Approximately two weeks prior to the study, the rabbit had a laser-induced lesion placed in the inferior temporal quadrant of the eye (darkened area at approx. 4:00) and just prior to the angiogram, a retinal vessel in the medullary ray had been occluded temporal to the disc by a focal application of 577 nm light from a dye-pumped argon laser. The excitation was 500 rn (50 nm bandwidth) and the filter used for the fluorescence image was 750 nm (10 nm bandwidth).

Figure 3:
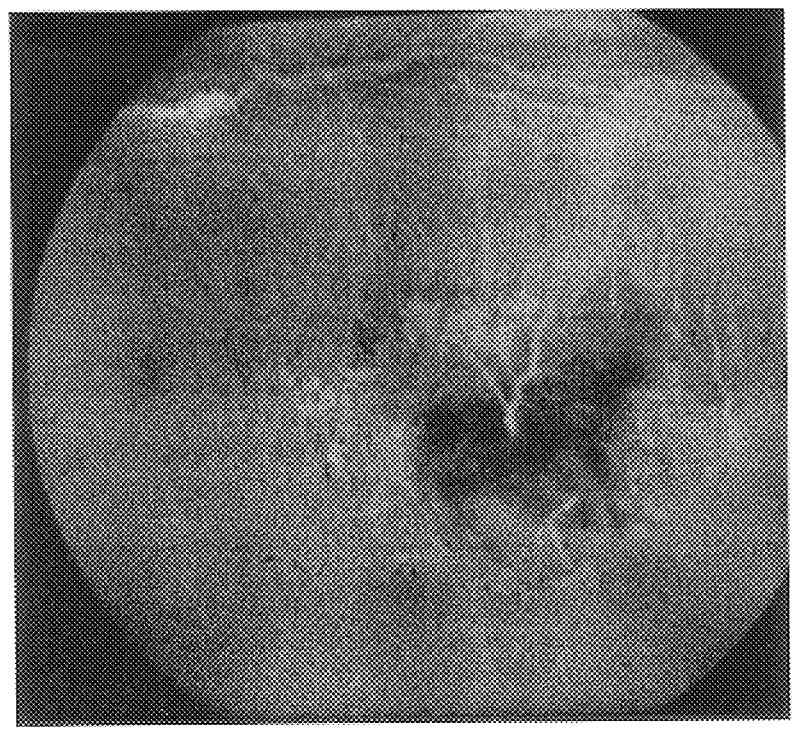
FIG. 3. Late phase LuT2BET fluorescent angiogram of the animal detailed in FIG. 2 revealing the occluded vessel in the upper left hand corner. Just off center the chronic lesion is easily visualized. Neovascular vessels are identified around an avascular scar.

The late LuT2BET angiogram is displayed in FIG. 3. An occluded retinal vessel with staining of the vessel wall is seen in the upper left of the angiogram and neovascularization around a relatively avascular area is seen in the lower right of the angiogram (the inferior temporal lesion noted in FIG. 2).

Figure 4:
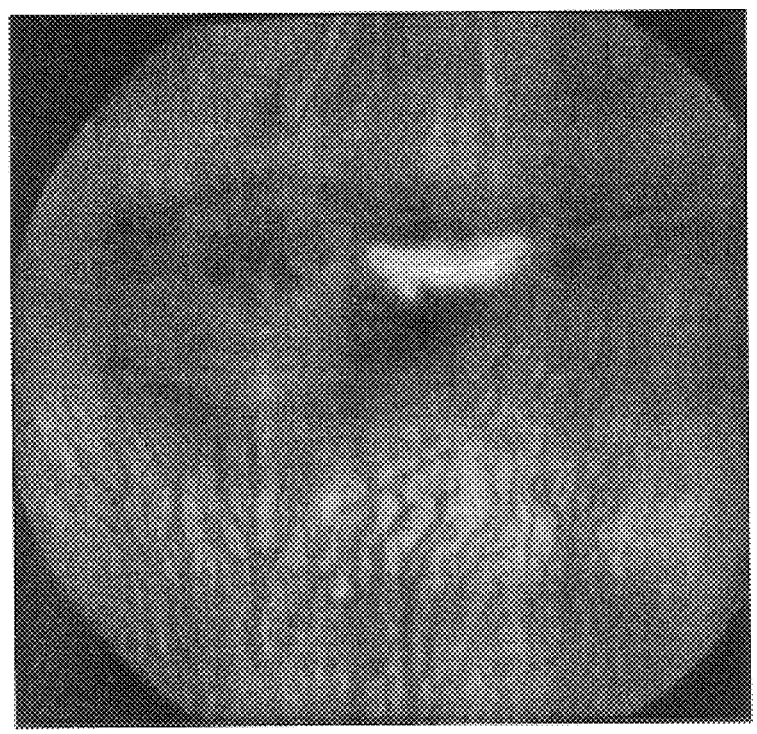
FIG. 4. Early stage fluorescein angiogram revealing leaking of the dye out of the acute lesion.
Figure 5:
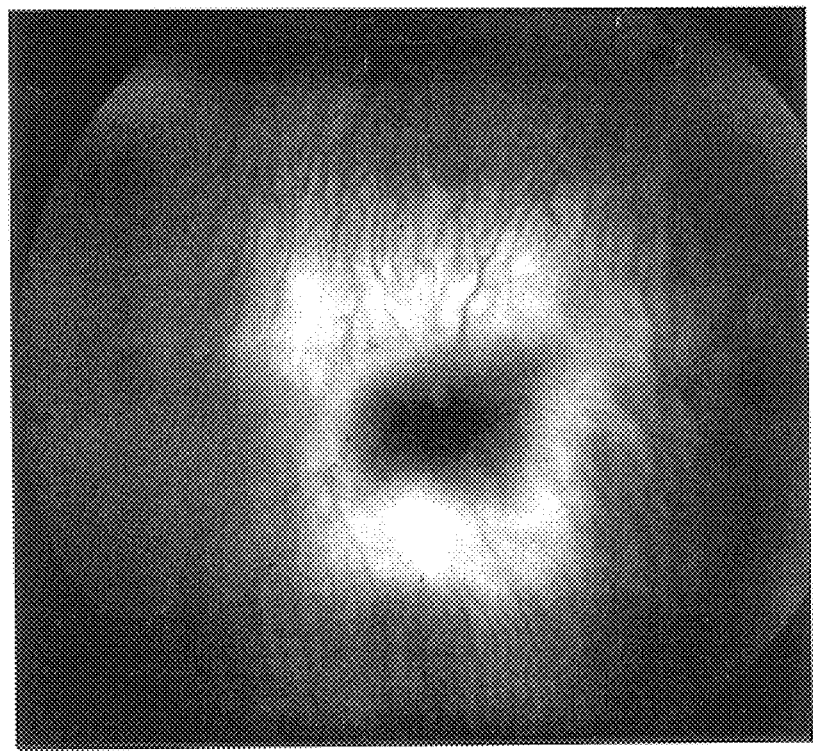
FIG. 5. Late stage fluorescein angiogram of the lower right hand quadrant of the animal in FIG. 4.

Early and late fluorescein angiograms are shown in FIG. 4 and FIG. 5, respectively. The damaged and induced neovascular lesions exhibited hyperfluorescence immediately after fluorescein injection followed by extensive leakage (FIG. 5).

Figure 6:
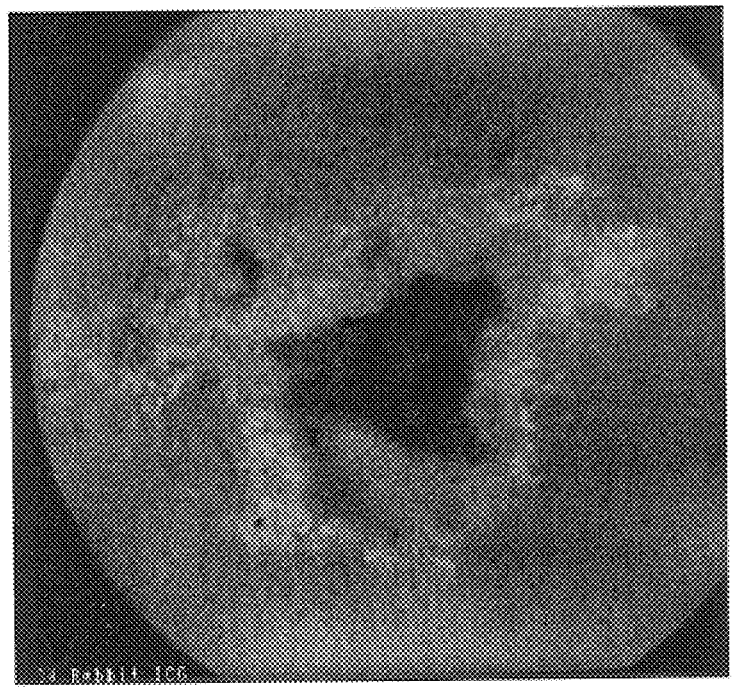
FIG. 6. Late stage ICG fluorescent angiogram of the lower right hand quadrant. The texaphyrin fluorescent angiogram of this same lesion is viewed in FIG. 3. The ICG image is amorphic and does not detail the neovascular vessels that are distinctly noted in FIG. 3.
Figure 7:
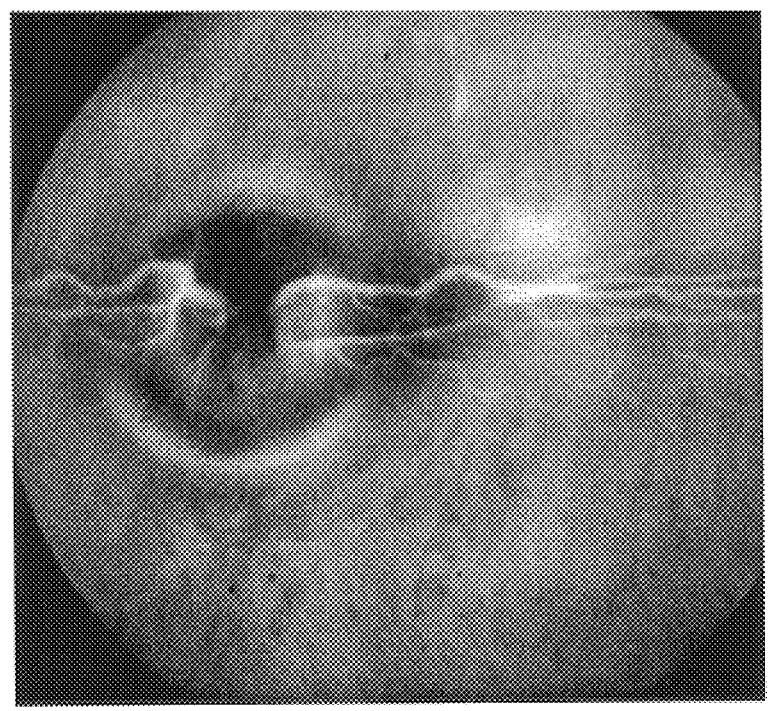
FIG. 7. Fluorescein angiogram of a rabbit's eye that had a lesion acutely induced in the medullary ray. The fluorescein is leaking from the laser-induced lesion.
Figure 8:
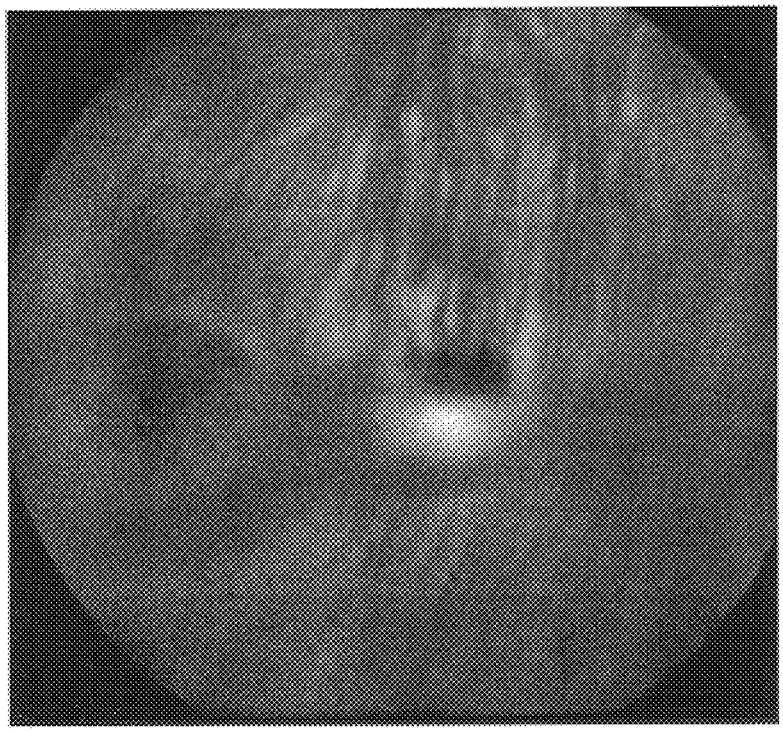
FIG. 8. Fluorescein angiogram of the rabbit in FIG. 7 after receiving PDT using LuT2BET. The image depicts closure of the vessels as evidenced by fluorescein staining and retention in the PDT targeted lesion.

FIG. 6 depicts the ICG angiogram of the laser-induced neovascular lesion (inferior temporal lesion, same region as in FIG. 3). The ICG has contrasted an arnorphic region, the vessels imaged with LuT2BET can not be delineated. FIG. 7 and FIG. 8 demonstrate fluorescein angiograms of a rabbit's eye having an induced lesion before and after receiving PDT with LuT2BET.

The concentration of LuT2BET in rabbit plasma after an intravenous injection of 1 $\mu$mol/kg was found to be 2.68 $\mu$g/ml at 15 min, 1.79 $\mu$g/ml at 30 min, 0.18 $\mu$g/ml at 3 hr, and 0.12 $\mu$g/ml at 5 h. The relative in vivo binding of LuT2BET to plasma protein components was assessed using density gradient ultracentrifugation. More sensitizer was associated with the HDL fraction (49%) compared to 40.5% for the heavy proteins, and 10.5% to the LDL portion.

The angiograms for ICG, fluorescein, and Lu(III)T2BET demonstrated different patterns of fluorescence. The retinal and choroidal vasculature of the rabbit were well delineated by LuT2BET angiography. Experimentally-induced retinal and choroidal vascular lesions were enhanced by LuT2BET and demonstrated subtly different patterns of staining than either fluorescein or ICG, consistent with the different wavelength employed and probable differential binding characteristics of LuT2BET. Fluorescein, a small molecule that is not bound to plasma elements, was diffusely present throughout the lesion with some central sparing in the ischemic/scarred zone. Indocyanine green, binding mainly to albumin, had a different fluorescence pattern than Lu(III)T2BET. Lu(III)T2BET, predominantly bound to lipoproteins and to some extent albumin, retained more angiographic information of the remaining vascular anatomy. These three agents reveal different features of ophthalmic disease. Histologic analysis revealed no evidence of retinal toxicity following photography.

FIG. 7 and FIG. 8 demonstrate fluorescein angiograms of a rabbit's eye having an induced lesion before and after receiving PDT with LuT2BET. Thirty minutes after injection with LuT2BET, laser light at 488 nm, spot size of 1000 μm, was directed to the lesion via a slitlamp lens system. Prior to PDT, fluorescence fluorescein angiography revealed some hyperfluorescence at early phases, which leaked over time (shown in FIG. 7). After PDT, the fluorescein angiogram revealed hyperfluorescence in the vessel (FIG. 8), indicative of reduced blood flow and therefore of vessel closure. There was limited fluorescence leakage outside of the PDT-treated vessel (compare FIG. 7 with FIG. 8).

These studies confirm that Lu(III)T2BET is capable of serving as a contrast agent for angiography of the eye, especially for visualizing the retinal and choroidal vascular systems, and as a photosensitive agent for photodynamic therapy of vascular lesions of the eye. Lu(III)T2BET demonstrated filling of retinal and choroidal vasculature, accumulation and fluorescence in areas of abnormal vasculature such as laser-induced choroidal neovascularization of the choroid and occlusive vasculopathy of the retina.

Closure of induced lesions was observed after PDT with LuT2BET. No damage to surrounding vessels or tissues was observed. Further, no damage was observed in control normal choroid or retinal tissue. The PDT treatment therefore demonstrated selectivity, an advantage over techniques, such as laser photocoagulation, for example.

Due to differences in solubility, partition coefficient, molecular weight, protein binding, and other variables, Lu(III)T2BET angiography results in different information than that obtained with either of the two most commonly used contrast agents, Na-fluorescein and indocyanine green. Additionally, Lu(III)T2BET has relatively more efficient energy-coupling capabilities than either agent. Lu(III)T2BET may be sequentially used advantageously for both angiography and PDT following a single or multiple adinistration.

The uses and methods disclosed and claimed herein can be executed without undue experimentation in light of the present disclosure. While the uses and methods of this invention have been described in terms of preferred embodiments, it will be apparent to those of skill in the art that variations may be applied to the uses and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for treating an ocular condition characterized by abnormal vasculature of a subject; the method comprising:

administering a photosensitive texaphyrin to the subject where the photosensitive texaphyrin has structure I:

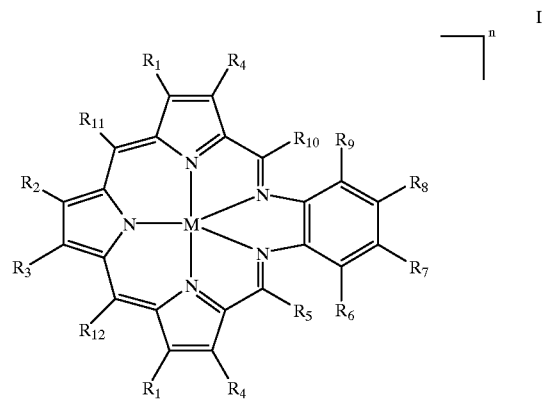

or structure II:

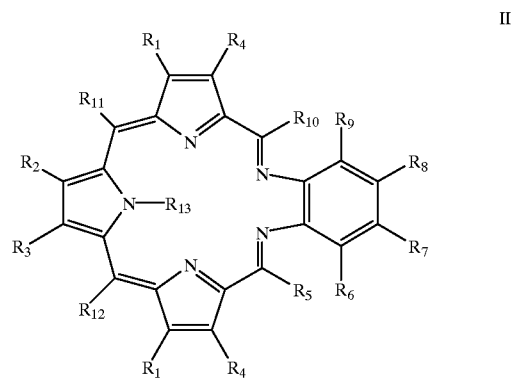

wherein

M is a diamagnetic metal cation;

$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, aminoalkyl, a site-directing molecule, a catalytic group, or a linker that is linked to a site-directing molecule or to a catalytic group;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, alkenyl, alkynyl, aryl, hydroxyalkyl, alkoxy, hydroxyalkoxy, hydroxyalkenyl, hydroxyalkynyl, carboxyalkyl, carboxyamide, carboxyamidealkyl, amino, aininoalkyl, or a linker that is linked to a saccharide, to a site-directing molecule, or to a catalytic group;

$R_{13}$ is alkyl, alkenyl, oxyalkyl, or hydroxyalkyl having up to about 3 carbon atoms and having rotational flexibility around a first-bound carbon atom; and n is an integer value less than or equal to 5 and photoirradiating the vasculature.

2. The method of claim 1 wherein the photosensitive texaphyrin is fluorescent and the treating is further in combination with observing the ocular condition of the subject by observing fluorescence of the texaphyrin.

3. The method of claim 1 wherein the ocular condition is selected from the group consisting of macular degeneration, glaucoma, disc neovascularization, retinal neovascularization, pannus, pterygium, retinal neovasculature, choroidal neovasculature, ocular histoplasmosis syndrome, myopia, ocular inflammatory disease, central serous retinopathy, subretinal neovascular membrane, and neovasculature induced by neoplasm.

4. The method of claim 1 wherein the ocular condition of the subject is macular degeneration.

5. The method of claim 1 wherein the photosensitive texaphyrin is bound to a diamagnetic metal cation and the diamagnetic metal cation is Lu(III), La(III), In(III), Zn(II) or Cd(II).

6. The method of claim 1 wherein the photosensitive texaphyrin is bound to a diamagnetic metal cation and the diamagnetic metal cation is Lu(III).

7. The method of claim 1 wherein the photoirradiating is with light having a wavelength range of about 700 to 800 nanometers.

8. The method of claim 1 wherein the photoirradiating is with light having a wavelength range of about 725–740 nanometers.

9. The method of claim 1 wherein the photosensitive texaphyrin is LuT2BET.

10. The method of claim 1 wherein the photosensitive texaphyrin has structure I.

11. The method of claim 10 wherein: $R_1$–$R_4$, $R_7$ and $R_8$ are independently alkyl, hydroxyalkyl, or hydroxyalkoxy; and $R_5$, $R_6$ and $R_9$–$R_{12}$ are hydrogen.

12. The method of claim 11 wherein $R_1$ is hydroxyalkyl; and $R_2$, $R_3$ and $R_4$ are alkyl.

13. The method of claim 1 wherein the photosensitive texaphyrin is administered by rapid infusion as a bolus.

14. The method of claim 13 comprising administering 0.01 to 5 µmol/kg of the photosensitive texaphyrin in a sterile aqueous or aqueous propylene glycol solution.

15. The method of claim 14 wherein the photosensitive texaphyrin is LuT2BET.

16. A method for observing vasculature in an eye of a subject, the method comprising:
administering a detectable texaphyrin to the subject; and
observing the vasculature of the eye
wherein the detectable texaphyrin has structure I:

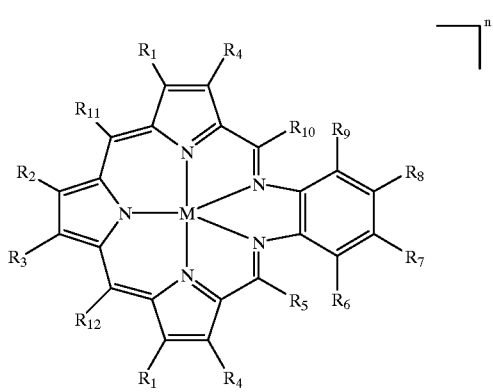

or structure II:

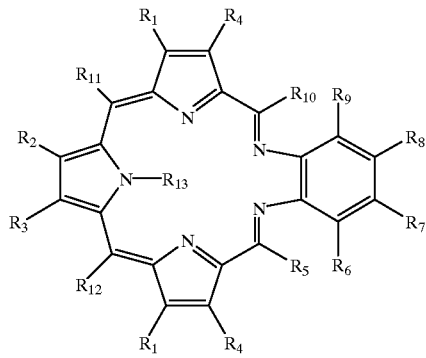

wherein

M is a diamagnetic metal cation;

$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, aminoalkyl, a site-directing molecule, a catalytic group, or a linker that is linked to a site-directing molecule or to a catalytic group;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, alkenyl, alkynyl, aryl, hydroxyalkyl, alkoxy, hydroxyalkoxy, hydroxyalkenyl, hydroxyalkynyl, carboxyalkyl, carboxyamide, carboxyamidealkyl, amino, aminoalkyl, or a linker that is linked to a saccharide, to a site-directing molecule, or to a catalytic group;

$R_{13}$ is alkyl, alkenyl, oxyalkyl, or hydroxyalkyl having up to about 3 carbon atoms and having rotational flexibility around a first-bound carbon atom; and n is an integer value less than or equal to 5.

17. The method of claim 16 where the detectable texaphyrin is fluorescent and the observing is by fluorescence.

18. The method of claim 17 where the fluorescent texaphyrin is in a metal complex with Y(III), Lu(III), or Gd(III).

19. The method of claim 17 where excitation light to induce fluorescence has a wavelength of about 400–500 nm.

20. The method of claim 17 where excitation light to induce fluorescence has a wavelength of about 700–800 nm.

21. The method of claim 16 wherein the detectable texaphyrin has structure I.

22. A method for observing and treating an ocular condition characterized by abnormal vasculature of a subject using a single agent, the method comprising
administering a photosensitive fluorescent texaphyrin to the subject;

observing the ocular condition of the subject by fluorescence of the texaphyrin; and
photoirradiating the vasculature
wherein the texaphyrin has structure I:

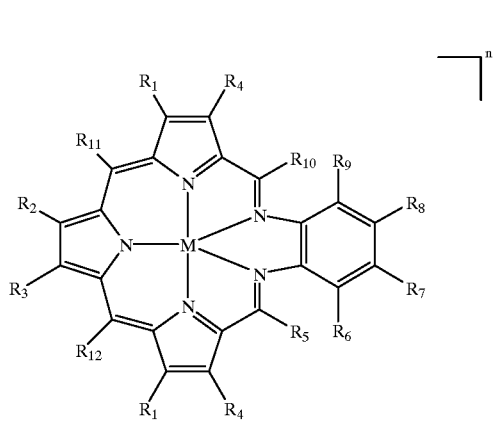

or structure II:

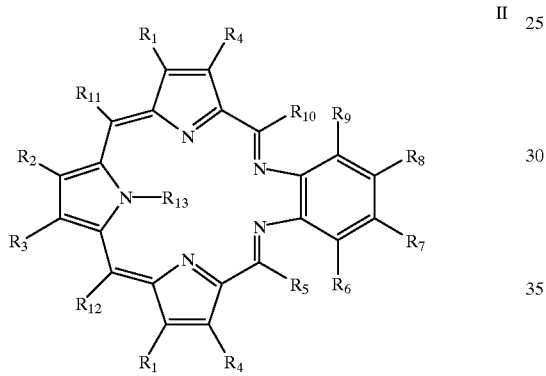

wherein
M is a diamagnetic metal cation;
$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, aminoalkyl, a site-directing molecule, a catalytic group, or a linker that is linked to a site-directing molecule or to a catalytic group;
$R_6$ and $R_9$ are independently selected from the groups of $R_1$–$R_4$, $R_7$ and R8, with the proviso that the halide is other than iodide and the haloalkyl is other than iodoalkyl;
$R_5$ and $R_{10}$–$R_{12}$ are independently hydrogen, alkyl, alkenyl, alkynyl, aryl, hydroxyalkyl, alkoxy, hydroxyalkoxy, hydroxyalkenyl, hydroxyalkynyl, carboxyalkyl, carboxyamide, carboxyamidealkyl, amino, aminoalkyl, or a linker that is linked to a saccharide, to a site-directing molecule, or to a catalytic group;
$R_{13}$ is alkyl, alkenyl, oxyalkyl, or hydroxyalkyl having up to about 3 carbon atoms and having rotational flexibility around a first-bound carbon atom; and
n is an integer value less than or equal to 5.
23. The method of claim 22 wherein the texaphyrin has structure I.

24. A method for photodynamic therapy of macular degeneration of a subject comprising:
administering a photosensitive texaphyrin to the subject where the photosensitive texaphyrin has structure I:

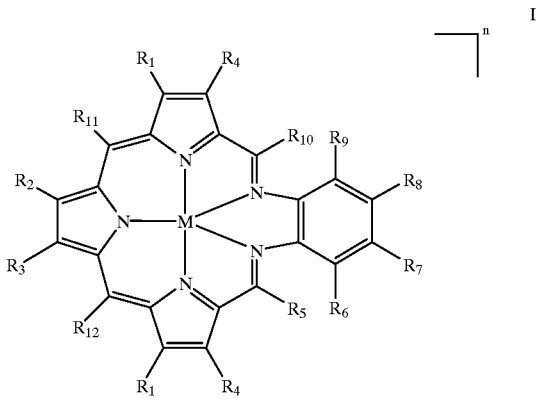

or structure II:

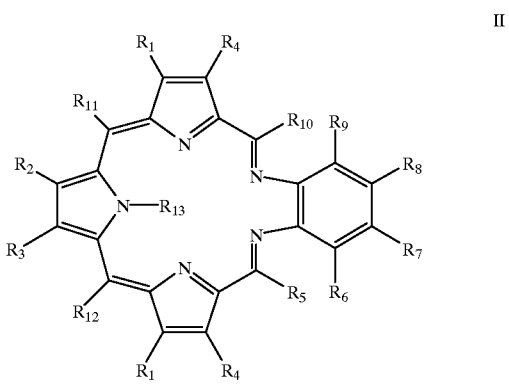

wherein
M is a diamagnetic metal cation;
$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, aminoalkyl, a site-directing molecule, a catalytic group, or a linker that is linked to a site-directing molecule or to a catalytic group;
$R_6$ and $R_9$ are independently selected from the groups of $R_1$–$R_4$, $R_7$ and $R_8$, with the proviso that the halide is other than iodide and the haloalkyl is other than iodoalkyl;
$R_5$ and $R_{10}$–$R_{12}$ are independently hydrogen, alkyl, alkenyl, alkynyl, aryl, hydroxyalkyl, alkoxy, hydroxyalkoxy, hydroxyalkenyl, hydroxyalkynyl, carboxyalkyl, carboxyamide, carboxyamidealkyl, amino, aminoalkyl, or a linker that is linked to a saccharide, to a site-directing molecule, or to a catalytic group;
$R_{13}$ is alkyl, alkenyl, oxyalkyl, or hydroxyalkyl having up to about 3 carbon atoms and having rotational flexibility around a first-bound carbon atom; and
n is an integer value less than or equal to 5 and photoirradiating the macula.

25. The method of claim 24 wherein the photosensitive texaphyrin is bound to a diamagnetic metal cation and the diamagnetic metal cation is Lu(III), La(III), In(III), Zn(II) or Cd(II).

26. The method of claim 24 wherein the photosensitive texaphyrin is bound to a diamagnetic metal cation and the diamagnetic metal cation is Lu(III).

27. The method of claim 24 wherein the photosensitive texaphyrin has structure I.

28. The method of claim 27 wherein: $R_1$–$R_4$, $R_7$ and $R_8$ are independently alkyl, hydroxyalkyl, or hydroxyalkoxy; and $R_5$, $R_6$ and $R_9$–$R_{12}$ are hydrogen.

29. The method of claim 28 wherein $R_1$ is hydroxyalkyl; and $R_2$, $R_3$ and $R_4$ are alkyl.

30. The method of claim 24 wherein the photosensitive texaphyrin is administered by rapid infusion as a bolus.

31. The method of claim 30 comprising administering 0.01 to 5 µmol/kg of the photosensitive texaphyrin in a sterile aqueous or aqueous propylene glycol solution.

32. The method of claim 31 wherein the photosensitive texaphyrin is LuT2BET.

* * * * *